United States Patent
Kermani et al.

(10) Patent No.: US 12,396,654 B2
(45) Date of Patent: Aug. 26, 2025

(54) RECONSTRUCTION AUGMENTATION BY CONSTRAINING WITH INTENSITY GRADIENTS IN MRI

(71) Applicant: Children's Medical Center Corporation, Boston, MA (US)

(72) Inventors: Ali Pouryazdanpanah Kermani, Brookline, MA (US); Onur Afacan, Brookline, MA (US); Simon K. Warfield, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 291 days.

(21) Appl. No.: 17/605,775

(22) PCT Filed: Apr. 24, 2020

(86) PCT No.: PCT/US2020/029712
§ 371 (c)(1),
(2) Date: Oct. 22, 2021

(87) PCT Pub. No.: WO2020/219803
PCT Pub. Date: Oct. 29, 2020

(65) Prior Publication Data
US 2022/0218222 A1    Jul. 14, 2022

Related U.S. Application Data
(60) Provisional application No. 62/838,452, filed on Apr. 25, 2019.

(51) Int. Cl.
*A61B 5/055* (2006.01)
*A61B 5/00* (2006.01)
(Continued)

(52) U.S. Cl.
CPC .......... *A61B 5/055* (2013.01); *A61B 5/7207* (2013.01); *G01R 33/5602* (2013.01); *G01R 33/5611* (2013.01)

(58) Field of Classification Search
CPC .. A61B 5/055; A61B 5/7207; G01R 33/5602; G01R 33/5611
See application file for complete search history.

(56) References Cited

U.S. PATENT DOCUMENTS

| 7,423,430 B1* | 9/2008 | Sharif ................ G01R 33/3415 |
| | | 324/309 |
| 9,524,567 B1 | 12/2016 | Brokish et al. |

(Continued)

FOREIGN PATENT DOCUMENTS

| WO | 2020078907 A1 | 4/2020 |
| WO | 2020219803 A1 | 10/2020 |

(Continued)

OTHER PUBLICATIONS

International Search Report and Written Opinion for International Application No. PCT/US2020/029712 mailed Jul. 9, 2020.

(Continued)

*Primary Examiner* — Dixomara Vargas
(74) *Attorney, Agent, or Firm* — Greenberg Traurig, LLP; Andrew J. Tibbetts; George E. Banis

(57) ABSTRACT

A method for imaging a tissue region of a patient includes receiving a plurality of magnetic resonance (MR) signals of the tissue region, each MR signal being measured by a corresponding one of a plurality of coils, each coil having a different spatial sensitivity profile; and generating an image of the tissue region based on the plurality of MR signals and the spatial sensitivity profile of each coil, including applying one or more constraints to the image generation, wherein at (Continued)

least one of the constraints couples a first image value to one or more neighboring image values.

20 Claims, 14 Drawing Sheets

(51) Int. Cl.
 *G01R 33/56* (2006.01)
 *G01R 33/561* (2006.01)

(56) References Cited

U.S. PATENT DOCUMENTS

| | | | |
|---|---|---|---|
| 2002/0039024 A1* | 4/2002 | Fuderer | G01R 33/5611 324/309 |
| 2005/0058368 A1* | 3/2005 | Moriguchi | G01R 33/285 324/309 |
| 2005/0189942 A1* | 9/2005 | Tsao | G01R 33/5611 324/309 |
| 2006/0261809 A1 | 11/2006 | Fuderer et al. | |
| 2010/0284595 A1 | 11/2010 | Mori et al. | |
| 2012/0082355 A1* | 4/2012 | Mendes | G01R 33/56509 382/131 |
| 2012/0249138 A1 | 10/2012 | Pfeuffer | |
| 2013/0076356 A1 | 3/2013 | Jellus et al. | |
| 2013/0229177 A1 | 9/2013 | Bammer et al. | |
| 2013/0249553 A1 | 9/2013 | Simonetti et al. | |
| 2013/0259343 A1* | 10/2013 | Liu | G06T 11/003 382/131 |
| 2013/0300414 A1* | 11/2013 | Guerin | G01R 33/288 324/309 |
| 2013/0320974 A1* | 12/2013 | Liu | G01R 33/5611 324/309 |
| 2014/0009156 A1 | 1/2014 | Doneva et al. | |
| 2014/0361770 A1* | 12/2014 | Dannels | G01R 33/34 324/309 |
| 2015/0065854 A1 | 3/2015 | Ahn et al. | |
| 2015/0369893 A1* | 12/2015 | Takeshima | G01R 33/5611 324/309 |
| 2016/0252596 A1 | 9/2016 | Nielsen et al. | |
| 2017/0325709 A1* | 11/2017 | Nayak | G01R 33/5601 |
| 2018/0024215 A1* | 1/2018 | Zhu | G01R 33/4835 324/309 |
| 2018/0232878 A1 | 8/2018 | Braun et al. | |
| 2018/0238986 A1* | 8/2018 | De Weerdt | A61B 5/055 |
| 2018/0238988 A1* | 8/2018 | Bernstein | G01R 33/561 |
| 2018/0260981 A1 | 9/2018 | Gholipour-Baboli et al. | |
| 2018/0306882 A1* | 10/2018 | Li | A61B 5/055 |
| 2019/0122398 A1* | 4/2019 | Huang | G06T 11/006 |
| 2019/0244399 A1* | 8/2019 | Li | G01R 33/56545 |
| 2021/0046329 A1 | 2/2021 | Lachaine et al. | |
| 2021/0196109 A1 | 7/2021 | Shelton, IV et al. | |

FOREIGN PATENT DOCUMENTS

| | | |
|---|---|---|
| WO | 2021099282 A1 | 3/2021 |
| WO | 2023004412 A1 | 1/2023 |
| WO | 2023027958 A1 | 3/2023 |
| WO | 2023034044 A1 | 3/2023 |

OTHER PUBLICATIONS

Wang et al., CONtrast Conformed Electrical Properties Tomography (CONCEPT) Based on Multi-Channel Transmission and Alternating Direction Method of Multipliers. IEEE Transactions on Medical Imaging, Author manuscript. PMC. Feb. 1, 2020:33 pages.

* cited by examiner

RECONSTRUCTION AUGMENTATION BY CONSTRAINING WITH INTENSITY GRADIENTS IN MRI

CROSS-REFERENCE TO RELATED APPLICATION

This application is a national stage filing under 35 U.S.C. 371 of International Patent Application Serial No. PCT/US2020/029712, filed Apr. 24, 2020, which claims priority to U.S. Provisional Patent Application No. 62/838,452, filed Apr. 25, 2019, the entire contents of which applications are incorporated herein by reference.

TECHNICAL FIELD

This description generally relates to image reconstruction techniques in magnetic resonance imaging.

BACKGROUND

Magnetic resonance imaging (MRI) typically uses a long scan time to acquire data used to reconstruct an image of a patient. Patient motion during the scanning process can lead to artifacts in the reconstructed image that reduce the image's diagnostic quality. Overall, the long scan time in MRI leads to expensive medical costs arising, e.g., from the slow rate of throughput of expensive capital equipment or from the use of sedation or anesthesia to reduce patient motion. Parallel imaging methods attempt to reduce the scan time of MRI by undersampling data used to reconstruct the image of the patient.

SUMMARY

In an aspect, a method for imaging a tissue region of a patient includes receiving a plurality of magnetic resonance (MR) signals of the tissue region, each MR signal being measured by a corresponding one of a plurality of coils, each coil having a different spatial sensitivity profile; and generating an image of the tissue region based on the plurality of MR signals and the spatial sensitivity profile of each coil, including applying one or more constraints to the image generation, wherein at least one of the constraints couples a first image value to one or more neighboring image values.

Embodiments can include one or more of the following features.

Generating the image includes solving a system of equations subject to the one or more constraints. Generating the image includes determining a least squares solution to the system of equations. Generating the image includes determining an augmented Lagrangian solution to the system of equations. The one or more constraints includes equality constraints in the system of equations.

Applying the one or more constraints includes applying a spatial derivative to the plurality of MR signals and the spatial sensitivity profile of each coil.

Applying the one or more constraints includes applying a filter to the plurality of MR signals and the spatial sensitivity profile of each coil.

Applying the one or more constraints reduces the geometry factor of the image.

The first image value is associated with a pixel or a voxel of the image.

The first image value is spatially adjacent to the one or more other image values in the image.

The method includes applying a magnetic field to the tissue region of the patient; generating an excitation RF pulse in the tissue region of the patient; and measuring MR signal from the tissue region with each of the plurality of coils to produce the plurality of MR signals. The method includes measuring the tissue region with an acceleration factor greater than or equal to two. The method includes measuring the tissue region in Cartesian space or in non-Cartesian space.

Applying the one or more constraints includes applying a spatial transformation to the plurality of MR signals.

At least one of the constraints couples a value of a first image generated from MR signals measured by a first subset of the plurality of coils to a value of a second image generated from MR signals measured by a second subset of the plurality of coils, the first subset of coils being different than the second subset of coils.

Applying the one or more constraints includes relating a first MR signal associated with a first contrast to a second MR signal associated with a second contrast.

In an aspect, a computing system includes one or more processors coupled to a memory, the processors and memory configured to receive a plurality of magnetic resonance (MR) signals of the tissue region, each MR signal being measured by a corresponding one of a plurality of coils, each coil having a different spatial sensitivity profile; and generate an image of the tissue region based on the plurality of MR signals and the spatial sensitivity profile of each coil, including applying one or more constraints to the image generation, wherein at least one of the constraints couples a first image value to one or more neighboring image values.

Embodiments can include one or more of the following features.

Generating the image includes solving a system of equations subject to the one or more constraints. Generating the image includes determining a least squares solution to the system of equations. Generating the image includes determining an augmented Lagrangian solution to the system of equations. The one or more constraints includes equality constraints in the system of equations.

Applying the one or more constraints includes applying a spatial derivative to the plurality of MR signals and the spatial sensitivity profile of each coil.

Applying the one or more constraints includes applying a filter to the plurality of MR signals and the spatial sensitivity profile of each coil.

Applying the one or more constraints reduces the geometry factor of the image.

The first image value is associated with a pixel or a voxel of the image.

The first image value is spatially adjacent to the one or more other image values in the image.

The one or more processors and memory are configured to apply a magnetic field to the tissue region of the patient; generate an excitation RF pulse in the tissue region of the patient; and measure MR signal from the tissue region with each of the plurality of coils to produce the plurality of MR signals. The one or more processors and memory are configured to measure the tissue region with an acceleration factor greater than or equal to two. The one or more processors and memory are configured to measure the tissue region in Cartesian space or in non-Cartesian space.

Applying the one or more constraints includes applying a spatial transformation to the plurality of MR signals.

At least one of the constraints couples a value of a first image generated from MR signals measured by a first subset of the plurality of coils to a value of a second image generated from MR signals measured by a second subset of the plurality of coils, the first subset of coils being different than the second subset of coils.

Applying the one or more constraints includes relating a first MR signal associated with a first contrast to a second MR signal associated with a second contrast.

In an aspect, a non-transitory computer readable medium stores instructions for causing a computing system to receive a plurality of magnetic resonance (MR) signals of the tissue region, each MR signal being measured by a corresponding one of a plurality of coils, each coil having a different spatial sensitivity profile; and generate an image of the tissue region based on the plurality of MR signals and the spatial sensitivity profile of each coil, including applying one or more constraints to the image generation, wherein at least one of the constraints couples a first image value to one or more neighboring image values.

Embodiments can include one or more of the following features.

Generating the image includes solving a system of equations subject to the one or more constraints. Generating the image includes determining a least squares solution to the system of equations. Generating the image includes determining an augmented Lagrangian solution to the system of equations. The one or more constraints includes equality constraints in the system of equations.

Applying the one or more constraints includes applying a spatial derivative to the plurality of MR signals and the spatial sensitivity profile of each coil.

Applying the one or more constraints includes applying a filter to the plurality of MR signals and the spatial sensitivity profile of each coil.

Applying the one or more constraints reduces the geometry factor of the image.

The first image value is associated with a pixel or a voxel of the image.

The first image value is spatially adjacent to the one or more other image values in the image.

The instructions cause the computing system to apply a magnetic field to the tissue region of the patient; generate an excitation RF pulse in the tissue region of the patient; and measure MR signal from the tissue region with each of the plurality of coils to produce the plurality of MR signals. The instructions cause the computing system to measure the tissue region with an acceleration factor greater than or equal to two. The instructions cause the computing system to measure the tissue region in Cartesian space or in non-Cartesian space.

Applying the one or more constraints includes applying a spatial transformation to the plurality of MR signals.

At least one of the constraints couples a value of a first image generated from MR signals measured by a first subset of the plurality of coils to a value of a second image generated from MR signals measured by a second subset of the plurality of coils, the first subset of coils being different than the second subset of coils.

Applying the one or more constraints includes relating a first MR signal associated with a first contrast to a second MR signal associated with a second contrast.

These and other aspects, features, and implementations can be expressed as methods, apparatus, systems, components, program products, methods of doing business, means or steps for performing a function, and in other ways, and will become apparent from the following descriptions, including the claims.

DESCRIPTION OF DRAWINGS

Like reference symbols in the various drawings indicate like elements.

DETAILED DESCRIPTION

Parallel imaging can be used to reduce scan time in magnetic resonance imaging (MRI) while mitigating distortion in the reconstructed image. In general, parallel imaging uses spatially varying coil sensitivity profiles from an array of receiver coils to reconstruct images despite undersampling of data. The undersampling allows for an accelerated MRI scan time, but also leads to a reduction in signal-to-noise ratio (SNR) and an increase in spatially varying artifact, known as the geometry factor, which arises due to uncompensated aliasing of the undersampled data. This artifact occurs even when the coil sensitivity profiles are known, as the artifact is associated with aliased data observed by multiple coils at locations where the coil sensitivity profiles are the same (or linear combinations of each other), and therefore do not allow for disambiguation. Further noise or uncertainty in the true value of the coil sensitivity profiles can increase the artifact. Thus, the extent of undersampling (and reduction in MRI scan time) that preserves high quality image reconstruction is limited in part by the total reduction in data associated with undersampling, and in part by the geometry factor that arises from the position of the coil array with respect to the anatomy being imaged. Known parallel imaging methods produce noisy reconstructed images with artifacts, and the reconstructed image quality degrades dramatically as data is increasingly undersampled.

The parallel imaging techniques described here apply one or more constraints to image reconstruction to reduce the geometry factor artifact that limits highly accelerated MRI acquisition. In particular, equality constraints are derived from the MRI acquisition model or otherwise identified and applied to the image reconstruction to induce a coupling between the signal intensity at a voxel, and the signal intensity at other voxels, such as neighboring voxels. These constraints can improve the conditioning of the parallel imaging reconstruction by disambiguating the aliasing artifact that arises from a variety of undersampling patterns. Further, the constraints can increase the SNR of the reconstructed image by reducing the effect of noise from individual coils on the final image. In this way, higher image quality can be achieved with increased undersampling factors, enabling more rapid acquisition of 2D and 3D MRI images, higher throughput in the operation of MRI systems, and ultimately reduced medical costs.

Figure 1:
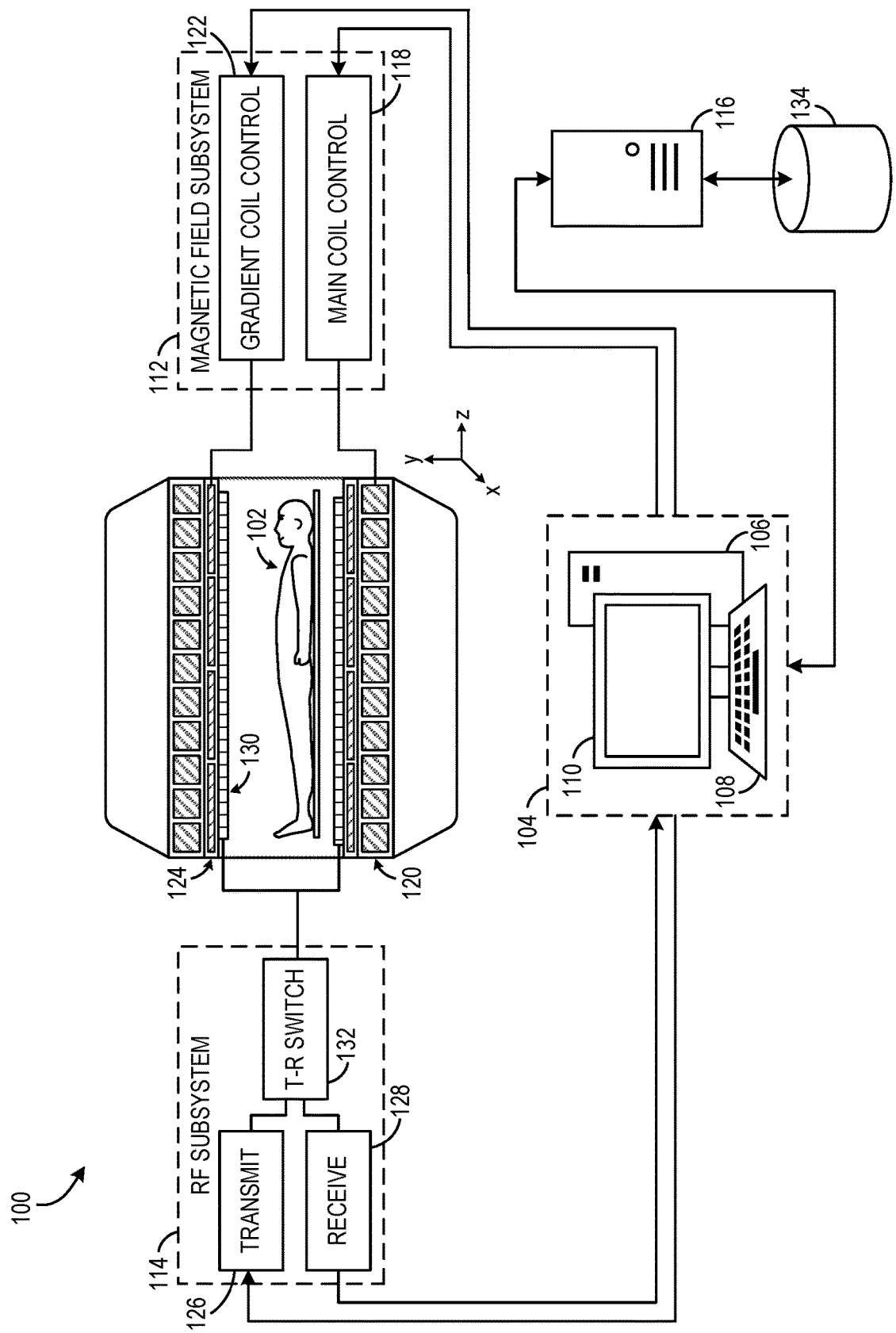
FIG. 1 is a schematic diagram of a magnetic resonance imaging (MRI) system.

FIG. 1 illustrates an example of a magnetic resonance imaging (MRI) system 100. In general, the MRI system 100 uses homogenous magnetic fields, magnetic field gradients, and radio frequency (RF) waves to induce nuclei in an object to be imaged, here a tissue region of a patient 102, to produce magnetic resonance (MR) signals. The MRI system 100 detects these MR signals and processes them in accordance with the techniques described here to produce one or more images of the tissue region.

As shown in FIG. 1, the MRI system 100 includes a workstation 104 that can communicate with various components and devices of the system 100 to carry out the imaging process. The workstation 104 includes one or more processors 106, one or more input devices 108, and a display 110. In some implementations, the workstation 104 can be or include a computer, a server, or another computing device, such as a laptop, a tablet, or a mobile device. In some implementations, the workstation 104 can be part of a distributed computing system having multiple local or remote computing devices coupled over a network. One or more wired or wireless communication channels can be established to enable communications between the workstation 104 and other components and devices in the MRI system 100, including a magnetic field subsystem 112, a RF subsystem 114, and a data processing server 116.

The magnetic field subsystem 112 includes a main coil controller 118 configured to control a main coil 120 and a gradient coil controller 122 configured to control one or more gradient coils 124. Each of the main coil controller 118 and the gradient coil controller 122 can include various hardware components, software components, or both, to cause the respective coils to produce one or more magnetic fields in accordance with instructions received from the workstation 104. For example, in some implementations, the main coil 120 or the gradient coils 124, or both, can be electromagnets, and the controllers 118, 122 can modulate the energizing current provided to the respective coils 120, 124 to control the strength of the magnetic field produced by each coil in accordance with instructions received from the workstation 104.

In general, the main coil 120 is used to produce a uniform and static magnetic field that is applied to the patient 102. Conventionally, the magnetic field produced by the main coil 120 is defined in the z-direction, as shown in FIG. 1. The gradient coils 124 can superimpose one or more additional magnetic fields onto the field produced by the main coil 120 in a selected direction, such as the x-, y-, or z-direction. In this way, the gradient coils 124 can produce magnetic gradients in the patient 102 that assist with spatial encoding of the MR signals obtained during the imaging process, as discussed below.

The RF subsystem 114 includes a RF transmitter 126 and a RF receiver 128, each of which is coupled to one or more RF coils 130. The RF transmitter 126 can be configured to produce a prescribed RF excitation field using some or all of the coils 130 in response to instructions received from the workstation 104. After the excitation field is applied to the patient 102, the RF receiver 128 uses some or all of the coils 130 to detect the responsive MR signals and provides the signals to the workstation 104. The RF transmitter 126 and the RF receiver 128 can be configured to share one or more of the coils 130 or can be coupled with separate transmit and receive coils 130, respectively. In some implementations, such as those where the RF transmitter 126 and the RF receiver 128 share the same coils 130, a transmit-receive switch 132 can be arranged to separate the transmitted RF excitation pulses and the received MR signals.

The MRI system 100 can include a wide range of individual RF coils 130 in a variety of arrangements. For example, in some implementations, the RF coils 130 can include one or more body coils, surface coils, or combinations of them, among others. A body coil is a coil with a homogenous sensitivity distribution that surrounds all or part of the patient 102. A surface coil is a coil positioned close to particular region of the patient 102, such as the tissue region to be imaged. Individually, a surface coil has a limited field of view (FOV) and an inhomogeneous spatial sensitivity profile that is highly sensitive in areas close to the coil and falls off rapidly with increasing distance from the coil.

In some implementations, such as when the MRI system 100 is used for parallel imaging, two or more surface coils can be arranged to form an array of RF coils 130. Each of the RF coils 130 in the array can have a different spatial sensitivity profile that is known by the MRI system 100 or determined by the system through a calibration process. The RF transmitter 126 can use some or all of the coils 130 in the coil array (or one or more separate transmit coils, such as a body coil) to produce the prescribed RF excitation field. The RF receiver 128 can be coupled with each of the coils 130 in the coil array and can use some or all of the coils to detect the responsive MR signals. In some implementations, each coil or set of coils in the coil array can be part of an independent receiver channel of the RF receiver 128. The MR signals detected in each channel are combined in accordance with the techniques described here to produce the final MR image.

In operation, the patient 102 is positioned within the MRI system 100. A magnetic field is applied to the patient 102 using the main coil controller 118 to align a small excess of magnetic dipole moments (nuclear or electron spins) in the tissue of the patient in the direction of the magnetic field. A series of gradient fields and RF excitation pulses having a desired frequency, phase, and amplitude are applied to the patient 102 using the gradient coil controller 122 and the RF transmitter 126 in accordance with a pulse sequence defined by the workstation 104. Typically, the frequency of the RF excitation pulses is chosen to be equal to the Larmor frequency of the dipole moments to bring the dipole moments into an excited state, thereby reorienting their magnetization. Other parameters of the pulse sequence can be determined by the workstation 104 based on, for example, user input into the workstation 104, information received during a prescan or calibration process carried out by the workstation 104, or information received from a previous scanning step, among others. In some implementations, the workstation 104 can receive information from one or more sensors connected to the patient 102, such as electrocardiogram sensors or respiratory sensors, and can use the information when determining the pulse sequence.

After the application of RF excitation pulses, the reoriented dipole moments will tend to return to a state of equilibrium in the magnetic field, emitting radiation in the process. The sequence of RF and gradient field pulses cause this radiation to be emitted as decaying MR signals that provide spatial information about the density or relaxation times, or both, of a certain type of nuclei, such as hydrogen nuclei, and the substance in which they occur. These MR signals are detected by the RF receiver 128 using some or all of the RF coils 130 and can be provided to the workstation 104. The MR signals can be processed locally by the workstation 104 or transmitted to the data processing server 116 for processing to reconstruct an image of the patient 102 in accordance with the techniques described here. The reconstructed images can be stored in a database 134 and presented on the display 110 for analysis of the internal structure of the patient 102.

Figure 2:
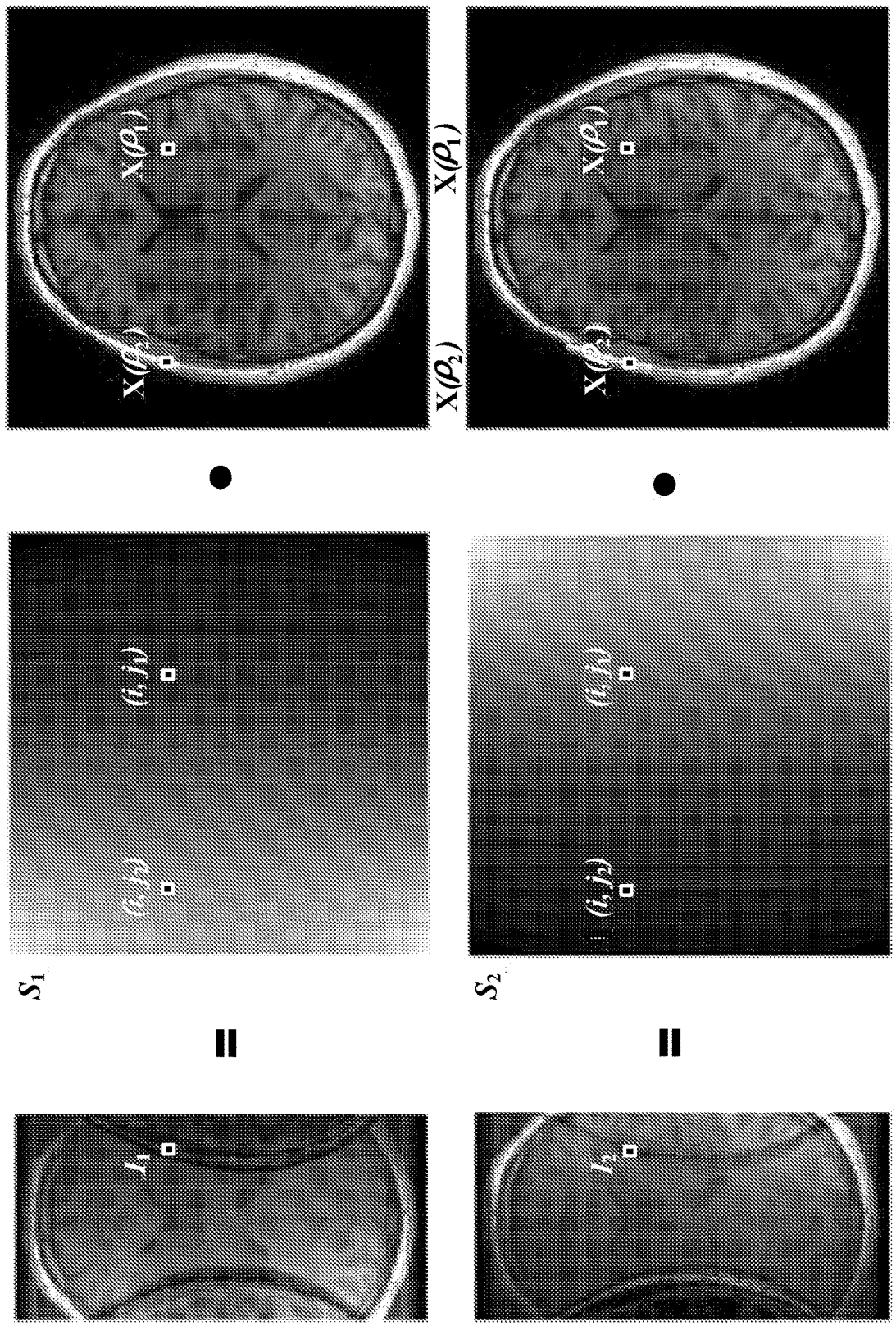
FIGS. 2 and 3 are diagrams of image reconstruction.

To reduce the acquisition time of the MRI system 100, parallel imaging methods can be used in which the imaging region of the patient 102 is undersampled and the spatial sensitivity profiles of the RF coils 130 are used to reconstruct the image. Referring to FIG. 2, an accelerated Cartesian acquisition, with undersampling rate R (sometimes referred to as the acceleration factor R), results in multiple, reduced FOV component coil images, some or all of which can include an aliasing artifact. Each pixel in an individual reduced FOV coil image can include information from multiple other pixels in the unknown full FOV image, which is to be estimated. The coil sensitivity S at the corresponding location in the full FOV can be used to weight these pixels. Therefore, the intensity in one pixel at a location received in the $k_{th}$ component coil image $I_k$ can be defined as:

$$I_k = \sum_{z=1}^{R} s_k(i, j_z) x(\rho_z) \quad (1)$$

We can rewrite equation (1) in matrix form as:

$$I = C_s x_p \quad (2)$$

Matrix $C_s$ denotes the sensitivities for each coil at the R superimposed positions and therefore has the dimension L×R (a 2×2 matrix in FIG. 2). The vector $x_\rho$ lists the R pixels (a 2×1 vector in FIG. 2) in the full field of view image. Accordingly, the scenario presented in FIG. 2 produces a system of equations having two equations, one for each receiver coil, and weights obtained by measuring the coil sensitivities. The system of equations can be solved for some locations, but at other locations the system of equations can exhibit linear dependence due to, for example, the coil sensitivity of each coil L being equal. If there are R or more such linearly independent equations, formed from the L coils, then the pixel values $x_\rho$ can be estimated. Typically, the system of equations can be solved by a least squares method. However, as R increases, the system of equations can fail to have full rank, and the image estimated by a pseudo-inverse least squares solution can exhibit spatially varying artifacts referred to as geometry factor artifacts. The geometry factor artifacts can be mitigated by restoring full rank to the system of equations. Thus, the fastest error-free acceleration factor R is limited by the maximum rank of the system of equations that can be obtained.

Figure 3:
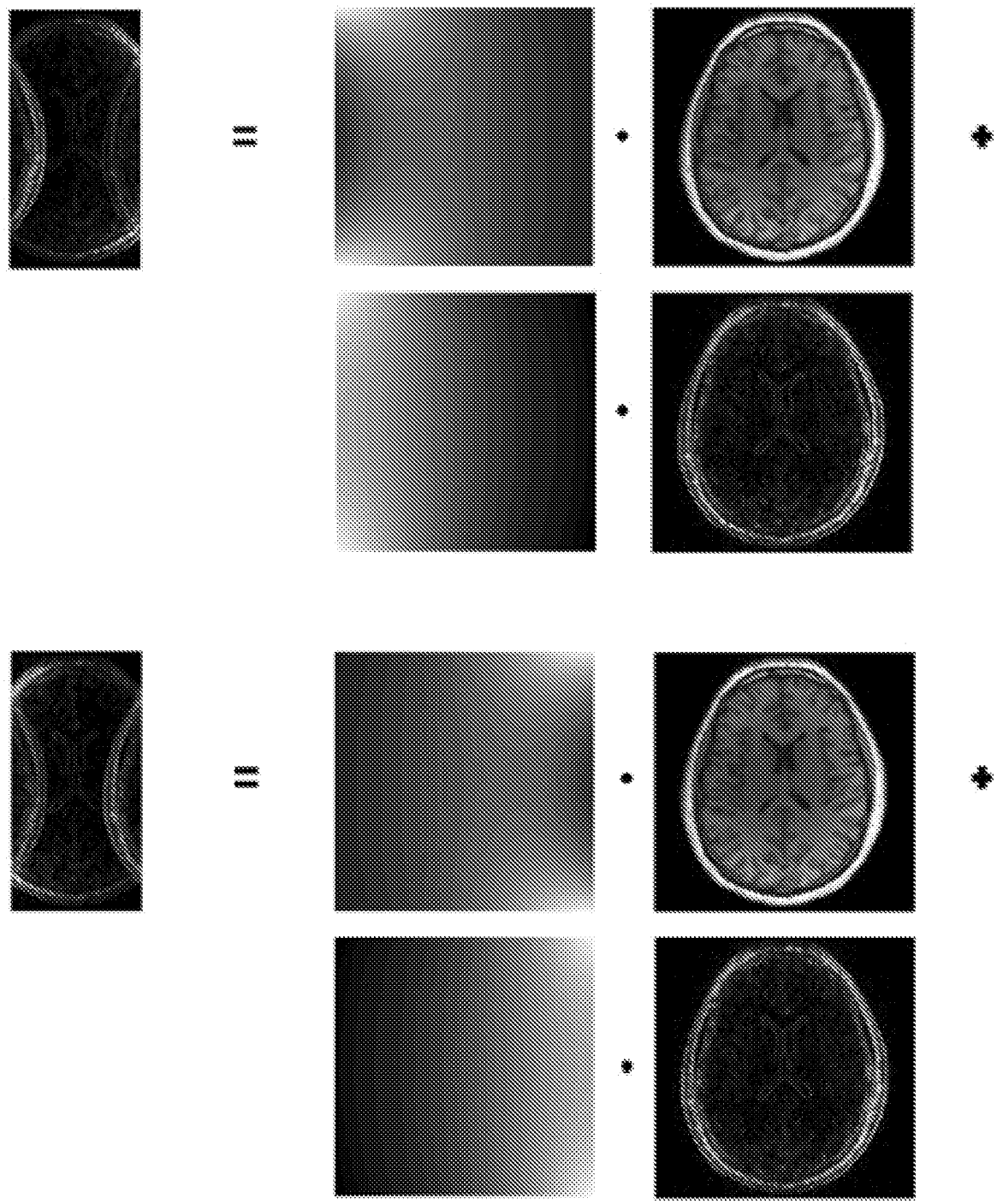

For example, consider an array of coils placed around a subject, each exhibiting a coil sensitivity profile that has a high sensitivity close to the coil, and that decays with an intensity related to the inverse of the square of the distance from the center of the coil. Even if the value of the coil sensitivity profile is equal for two or more coils, at such locations, the orientation of the decay of the coil sensitivity profile is different for each coil, and even at spatial locations where the coil profiles are equal at two or more coils, the orientation of the coil profiles are distinct. Therefore, the gradient of the coil sensitivity profile can be exploited to increase rank of the reconstruction matrix and to reduce the occurrence of geometry factor artifact. The spatial gradient of the system of equations can be computed to obtain a new constraint that is be valid for any reconstructed image. FIG. 3 illustrates the new constraint that holds.

The complete MR imaging model can be defined as:

$$d_l(k_m) = \int S_l(\rho) x(\varphi e^{-i2\pi k_m \rho} d\rho + n_l(k_m) \quad (3)$$

where $d_l(k_m)$ is the data-samples measurements from $l_{th}$ coil at the $m_{th}$ k-space location $k_m$. $n_l(k_m)$ is the noise measured from $l_{th}$ coil at the $m_{th}$ k-space location. $x(\varphi$ is the samples of unknown MR image to be recovered. $S_l$ is the sensitivity map of the $l_{th}$ coil. The following MR imaging model in Equation (3) can be rewritten in discretized form as:

$$d = Ex + n \quad (4)$$

where x is the samples of unknown MR image, E=FS is an encoding matrix, and F is an undersampled Fourier matrix. $S=[S_1 \ldots S_L]$, $S_l$ is a matrix representing the sensitivity map of the $l_{th}$ coil, $1 \leq l \leq L$, and L is the total number of coils.

Assuming without loss of generality that the inter-coil noise covariance has been whitened, the imaging model can be solved and the optimal maximum likelihood estimate for x can be reached when E has full column rank. This can be done by solving the least squares problem.

$$\hat{x} = (E^H E)^{-1} E^H d \quad (5)$$

In a case of undersampled k-space data, Equation (5) can yield artifacts depending on the sampling pattern. If Cartesian-type sampled k-space is used, then aliasing artifacts can be created in the coil images. Estimates of the image using Equation (5) can be achieved using least-squares, but geometry factor artifacts can arise due to the ambiguity inherent in the coil sensitivity profiles. This can occur even when the coil sensitivity profiles are known exactly, as the ambiguity is associated with aliased data observed by multiple coils at locations where the coil sensitivity profiles are the same, and therefore do not allow for disambiguation. Additional noise or uncertainty in the true value of the coil sensitivity profiles can increase the extent of the artifacts.

The techniques described here can improve the reconstruction accuracy by extending the reconstruction equations using additional constraints. For example, a plurality of MR signals of a tissue region of a patient can be received, each MR signal being measured by a corresponding one of a plurality of coils, each coil having a different spatial sensitivity profile. An image of the tissue region can be generated based on the plurality of MR signals and the spatial sensitivity profile of each coil, including applying one or more constraints to the image generation. At least one of the constraints can couple a first image value, such as a signal intensity of a pixel or voxel of the image, to one or more other image values, such as neighboring image values.

The constraints can be extracted from, for example, first-order and/or second-order derivatives of Equation (4), although other constraints are possible as discussed below. For example, consider the application of a derivative operator, such as a partial derivative of a Gaussian kernel, or a finite difference operator, to the left hand side and right hand side of Equation (4). First order partial derivatives, in the x-, y-, or z-direction, can be taken, and in addition, second order partial derivatives of each of the first order partial derivatives can be taken. Applying a derivative operator on the right-hand side leads to a term involving the derivative of the coil sensitivity profiles and a term involving the derivative of the unknown image x. When the unknown true image can be estimated from Equation (4), it also holds that the derivative of the left hand side is equal to the derivative of the right hand side. The expressions arising from the application of derivative operators can be expressed as equality constraints that hold at the solution to Equation (4). The solution of the system of equations can be arrived at through numerical techniques such as the penalized likelihood method or an Augmented Lagrangian formulation, among others. When the coil sensitivity profiles are known or estimated from, for example, autocalibration data, the explicit derivatives can be calculated. According to the Biot-Savart Law, the coil sensitivity profiles are expected to have a smooth profile that falls off with distance squared, and consequently third or higher order spatial derivatives of the coil profiles are expected to go to zero. Consequently, while first and second order derivatives couple additional information about the unknown image x across either of the coil sensitivity profiles or positions in space, third derivatives can not do so.

For example, consider the ideal scenario of no noise. Taking the inverse Fourier transform of both the left hand side and the right hand side of Equation (4) and then considering the spatial derivative of the coil image in the x direction yields the following equations:

$$\frac{\partial}{\partial x} a_j(x, y) = \frac{\partial}{\partial x}\left(\sum_{r=0}^{N_a-1} p(x, y+rL/R) \cdot C_j(x, y+rL/R)\right) \quad (5)$$

$$\frac{\partial}{\partial x} a_j(x, y) = \sum_{r=0}^{N_a-1}\left(\frac{\partial}{\partial x} p(x, y+rL/R) \cdot C_j(x, y+rL/R)\right) \quad (6)$$

$$\frac{\partial}{\partial x} a_j(x, y) = \sum_{r=0}^{N_a-1}\left(p(x, y+rL/R) \cdot \frac{\partial}{\partial x} C_j(x, y+rL/R) + C_j(x, y+rL/R) \cdot \frac{\partial}{\partial x} p(x, y+rL/R)\right) \quad (7)$$

where a(x,y) is a vector of j coil images (expressed as a 2D image for simplicity) formed by the inverse Fourier transform of the measured k-space data d; p(x,y) represents the unknown image to be recovered, denoted as x in Equation (4); $C_j(x,y)$ is the coil sensitivity profile denoted as $S_l$ following Equation (4); $N_a$ is the number of aliased voxels that overlap due to the undersampling; and L represents the full field of view.

The first spatial derivative of the coil profile $C_j(x)$ in the x direction, denoted $C_j'^{,x}(x, y)$, can be computed numerically from knowledge of $C_j(x, y)$. Furthermore, the observed data $a_j(x,y)$, denoted $a_j'^{,x}(x,y)$, can be numerically differentiated, for example, by convolution with a numerical approximation to the derivative operator. Therefore:

$$a_j'^{,x}(x, y) = \sum_{r=0}^{N_a-1}\left(p(x, y+rL/R) \cdot C_j'^{,x}(x, y+rL/R) + C_j(x, y+rL/R) \cdot \frac{\partial}{\partial x} p(x, y+rL/R)\right) \quad (8)$$

$$a_j'^{,x}(x, y) = \left(\sum_{r=0}^{N_a-1} p(x, y+rL/R) \cdot C_j'^{,x}(x, y+rL/R)\right) + \left(\sum_{r=0}^{N_a-1} C_j(x, y+rL/R) \cdot \frac{\partial}{\partial x} p(x, y+rL/R)\right) \quad (9)$$

The derivative operator operating on the unknown image p(x,y) can be approximated numerically. One example of an approximation is a central difference approximation:

$$\frac{\partial}{\partial x} p(x, y+rL/R) \approx 0.5 \cdot (p(x+1, y+rL/R) - p(x-1, y+rL/R)) \quad (10)$$

Substituting the derivative approximation from Equation (10) into Equation (9) produces Equation (11), which can be rewritten as shown in Equation (12):

$$a_j'^{,x}(x, y) = \left(\sum_{r=0}^{N_a-1} p(x, y+rL/R) \cdot C_j'^{,x}(x, y+rL/R)\right) + \left(\sum_{r=0}^{N_a-1} C_j(x, y+rL/R) \cdot 0.5 \cdot (p(x+1, y+rL/R) - p(x-1, y+rL/R))\right) \quad (11)$$

$$a_j'^{,x}(x, y) = \left(\sum_{r=0}^{N_a-1} p(x, y+rL/R) \cdot C_j'^{,x}(x, y+rL/R) + 0.5\right) \cdot \left(\sum_{r=0}^{N_a-1} p(x+1, y+rL/R) \cdot C_j(x, y+rL/R) - 0.5\right) \cdot \left(\sum_{r=0}^{N_a-1} p(x-1, y+rL/R) \cdot C_j(x, y+rL/R)\right) \quad (12)$$

Equation (12) expresses a relationship between voxel values at aliased locations, and on adjacent rows, with weights that depend on the known coil sensitivity profiles at adjacent locations, and on the rate of change of the coil sensitivity profile. No assumptions about the true image, except that it can be numerically differentiated, are made, so this relationship holds for any object being imaged.

It is important to note also that the derivative of the least squares estimate of the image is not equal to the derivative of the true image, due to the appearance of a geometry factor artifact in the least squares estimate. Equation (12) provides a relationship between the voxel values at other locations that holds for the true image, but which does not hold if the least square estimate of the image is substituted for the true image. Rather, this relationship is a constraint that can inform the estimation of the true image. When the spatial information provides new independent information (such as occurs if the true image content varies in space or the coil sensitivity profiles are differently oriented in space around the object), the least squares estimate of the image subject to this constraint is a better approximation of the true image than the least squares estimate without this constraint.

In general, some numerical derivative operators may provide better constraints than others. For example, longer numerical derivative approximations couple voxels further apart in space, and may better exploit the variation in the coil sensitivity profile in space.

For example, consider a derivative operator of length m for computing the spatial derivative along an axis:

$$[d_1, d_2, \ldots, d_m]^T \quad (13)$$

By constructing a Toeplitz matrix D with columns that are shifted copies of the discrete derivative operator, the derivative of the unknown image p can be expressed as Dp.

Rewriting the system of equations formed by the spatial derivative of the coil images (e.g., Equation (7)) in matrix form, and using the Toeplitz matrix D for the discrete spatial derivative operator, we find:

$$D[a_j] = (D[C_j]) \cdot p + [C_j] \cdot (Dp) \quad (14)$$

$$D[a_j] = (D[C_j]) \cdot p + ([C_j] \cdot D) \cdot p \quad (15)$$

$$D[a_j] = (D[C_j] + [C_j] \cdot D) \cdot p \quad (16)$$

Therefore, a constrained least squares estimator can be expressed as:

$$\hat{p} = \min_{p} \|(a - Cp)\|^2 \tag{17}$$

Subject to the constraint that the solution satisfy:

$$D[a]=(D[C]+[C]\cdot D)\cdot p \tag{18}$$

It is also possible to incorporate a regularizer if desired by defining $\hat{p}=$ $$\min_{p}\|(a - Cp)\|^2 + \Psi(p)$$

such that, $D[a]=(D[C]+[C]\cdot D)\cdot p$, although the techniques described here do not require regularization.

This equality constraint arises from the assumption that the spatial derivative of each aliased coil image can be computed, and relates the spatial derivative of the aliased coil image to the spatial derivative of the unknown true image through the coil sensitivity profiles. This relationship is expected to hold for all objects undergoing imaging, and does not require any additional assumptions about the nature of the image. Since both the coil sensitivity profiles and the aliased coil images are obtained from acquired data, and because the spatial derivative operator can be selected ahead of time, this equation relates a property of the measured data to properties of the unknown true image in a manner that further constrains the estimator so that the residual error $\epsilon = \|p - \hat{p}\|$ is smaller than it would be without the constraint. This mitigates the geometry factor artifact and facilitates higher acceleration.

Although the formulation described above uses a single spatial derivative, the techniques described here can be generalized to more than one spatial derivative and to higher order derivatives, each of which can provide additional constraints. Further, while use of a spatial derivative may be advantageous because the spatial derivative of the coil sensitivity profiles can be computed with great accuracy, other spatial constraints can be used in some implementations. The above explanation is also simplified by the assumption of Cartesian sampling, but the techniques described here are not limited to Cartesian sampling and can be applied in non-Cartesian sampling as well. Similarly, although the above explanation focuses on an image-space solution, it is possible to formulate an analogous solution in k-space.

The least squares solution that satisfies the equality constraint(s) can be obtained using several different numerical methods. One approach is to use a penalty method. Another approach is to use an augmented Lagrangian formulation, which may result in faster convergence and greater stability at large values of the penalty parameter, relative to the penalty method. Examples of such an augmented Lagrangian formulation are described below.

As non-limiting examples, three other formulations of the reconstruction equations are presented: Model 1 (Equation (19)) includes constraint optimization exploiting first-order derivative information, Model 2 (Equation (20)) includes constraint optimization exploiting second-order derivative information, and Model 3 (Equation (21)) includes constraint optimization exploiting both first- and second-order derivative information.

$$\underset{x, u_0}{\text{minimize}} \; g_0(x, u_0) \text{ subject to } u_0 = Dd_I - DSx - SDx \tag{19}$$

$$\underset{x, u_0}{\text{minimize}} \; g_0(x, u_0) \text{ subject to } u_0 = D_2 d_I - D_2 Sx - 2DSDx - SD_2 x \tag{20}$$

$$\underset{x, u_0, u_1}{\text{minimize}} \; g_0(x, u_0, u_1) \text{ subject to } u_0 = Dd_I - DSx - SDx, \tag{21}$$

$$u_1 = D_2 d_I - D_2 Sx - 2DSDx - SD_2 x$$

where D includes first-order finite difference operators, $D_2$ includes second-order finite difference operators, $d_I = F^H d$, and $$g_0(x,u_0)=\tfrac{1}{2}\|d-FSx\|_2^2+\beta\|u_0\|_p, g_1(x,u_0,u_1)=\tfrac{1}{2}\|d-FSx\|_2^2+\beta_1\|u_0\|_p+\beta_2\|u_1\|_p \tag{22}$$

where $\|\cdot\|_p$ is $l_p$-norm. In order to solve the reconstruction problem based on the proposed framework, the constraint equations can be solved iteratively using, for example, an Augmented Lagrangian method, as discussed below.

In some implementations, an Augmented Lagrangian framework can be used to solve each of the optimization models with linear equality constraints in the form of:

$$\hat{q} = \underset{q}{\text{argmin}} \; g(q) \text{ subject to } Cq = h \tag{23}$$

where g is a convex function, and the constraint equations are specified in C and h. The Augmented Lagrangian function for the previous problem can be defined as:

$$\mathcal{L}(q, \alpha, \mu) = g(q) + \alpha^H(Cq - h) + \frac{\mu}{2}\|Cq - h\|_2^2 \tag{24}$$

where $\alpha$ is Lagrange multipliers vector, and $\mu$ controls the impact of the constraints on $\mathcal{L}$. A solution for Equation (23) can be achieved by alternating between the two following equations until some stopping criterion is satisfied:

$$q^{(j+1)}=\arg_q \min \mathcal{L}(q,\alpha^{(j)},\mu) \tag{25}$$

$$\alpha^{(j+1)}=\alpha^{(j)}=\mu(Cq^{(j+1)}-h) \tag{26}$$

Thus, the Augmented Lagrangian function in Equation (24) can be rewritten by grouping together the terms as:

$$\mathcal{L}(q, \gamma, \mu) = g(q) + \frac{\mu}{2}\|Cq - \gamma\|_2^2 + C_\alpha \text{ where } \gamma = h - \left(\frac{1}{\mu}\right)\alpha, \tag{27}$$

and $C_\alpha$ can be ignored since it is independent of q.

The Augmented Lagrangian framework can be used to solve the reconstruction problems presented in each of Models 1, 2, and 3. Beginning with Model 1, the reconstruction problem can be formulated in a penalized-likelihood setting:

$$\underset{x, u_0, u_1 \cdot u_2}{\text{minimize}} \; g_0(u_0, u_1) \text{ subject to } u_0 = Sx, \tag{28}$$

$$u_1 = Dd_I - DSu_2 - SDu_2, u_2 = x$$

$u_2$ is defined to decouple $u_0$ and $u_1$, and $$g(u_0,u_1)=\tfrac{1}{2}\|d-Fu_0\|_2^2+\beta\|u_1\|_p \tag{29}$$

The minimization problem can be rewritten in the general Augmented Lagrangian framework defined in Equation (23) as:

$$u = \begin{bmatrix} u_0 \\ u_1 \\ u_2 \\ x \end{bmatrix}$$

$$g(q) = g(u_0, u_1), \quad C = GB$$

$$b = \begin{bmatrix} 0 \\ Dd_I \\ 0 \end{bmatrix}$$

$$G = \begin{bmatrix} I_{N_1} & 0 & 0 \\ 0 & \sqrt{v_1} I_D & 0 \\ 0 & 0 & \sqrt{v_2} I_{N_2} \end{bmatrix}$$

$$B = \begin{bmatrix} I_{N_1} & 0 & 0 & -S \\ 0 & I_D & L_2 & 0 \\ 0 & 0 & I_{N_2} & -I_{N_2} \end{bmatrix}$$

where $L_2 = SD + DS$. Matrix G is a diagonal weighting matrix, and $v_{1,2} > 0$. The Augmented Lagrangian function in Equation (24) can be defined by:

$$\mathcal{L}(u, \alpha, \mu) = g(u_0, u_1) + \alpha^H(GBu - b) + \frac{\mu}{2}\|Bu - b\|_2^2 \quad (30)$$

where $\alpha_2 = [\alpha_0^H \alpha_1^H \alpha_2^H]_H$, and $a_0$, $a_1$, and $a_2$ correspond to each row of B. The Augmented Lagrangian function $\mathcal{L}$ can be rewritten in the form of Equation (27) as:

$$\mathcal{L}(u, \gamma, \mu) = g(u_0, u_1) + \frac{\mu}{2}\|Bu - \gamma\|_2^2 \text{ where} \quad (31)$$

$$\gamma = [\gamma_0^H \gamma_1^H \gamma_2^H]^H = b - \left(\frac{1}{\mu}\right) G^{-1} \alpha.$$

By applying an alternating minimization method, the following subproblems can be produced:

$$u_0^{(j+1)} = \underset{u_0}{\operatorname{argmin}} \frac{1}{2}\|d - Fu_0\|_2^2 + \frac{\mu}{2}\|u_0 - Sx^{(j)} - \gamma_0^{(j)}\|_2^2 \quad (32)$$

$$u_1^{(j+1)} = \underset{u_1}{\operatorname{argmin}} \beta\|Dd_I - DSu_2^{(j)} - SDu_2^{(j)}\|_p + \quad (33)$$
$$\frac{\mu v_1}{2}\|u_1 - (Dd_I - DSu_2^{(j)} - SDu_2^{(j)}) - \gamma_1^{(j)}\|_2^2$$

$$u_2^{(j+1)} = \underset{u_2}{\operatorname{argmin}} \frac{\mu v_1}{2}\|u_1^{(j+1)} - (Dd_I - DSu_2 - SDu_2) - \gamma_1^{(j)}\|_2^2 + \quad (34)$$
$$\frac{\mu v_2}{2}\|u_2 - x^{(j)} - \gamma_2^{(j)}\|_2^2$$

$$x^{(j+1)} = \underset{x}{\operatorname{argmin}} \frac{\mu}{2}\|u_0^{(j+1)} - Sx - \gamma_0^{(j)}\|_2^2 + \frac{\mu v_2}{2}\|u_2^{(j+1)} - x^{(j)} - \gamma_2^{(j)}\|_2^2 \quad (35)$$

The minimization cost function in Equation (33) with respect to $u_1$ can be solved based on the shrinkage rule as $$u_1^{(j+1)} = \operatorname{shrink}\left(u_1^{(j)} + \gamma_1^{(j)}, \frac{\lambda}{\mu}\right) \quad (36)$$

where $$\operatorname{shrink}(z, Th) = \frac{z}{\|z\|_2}\max\{\|z\|_2 - Th, 0\} \quad (37)$$

The minimization cost functions in Equations (32), (34), and (35) are all quadratic and have closed-form solutions for $u_0$, $u_2$, and $x$ as follows:

$$u_0^{(j+1)} = H_\mu^{-1}[F^H d + \mu(Sx^{(j)} + \gamma_0^{(j)})] \quad (38)$$

$$u_2^{(j+1)} = H_{v_1 v_2}^{-1}[v_1(D^H S^H + S^H D^H)(Dd_I - u_1^{(j+1)} + \gamma_1^{(j)}) + v_2(x^{(j)} + \gamma_2^{(j)})] \quad (39)$$

$$x^{(j+1)} = H_{v_2}^{-1}[S^H(u_0^{(j+1)} - \gamma_0^{(j)}) + v_2(u_2^{(j+1)} - \gamma_2^{(j)})] \quad (40)$$

where $$H_\mu = F^H F + \mu I_{N_1} \quad (41)$$

$$H_{v_1 v_2} = v_1(D^H S^H DS + D^H S^H SD + S^H D^H DS + S^H D^H SD) + v_2 I_{N_2} \quad (42)$$

$$H_{v_2} = S^H S + v_2 I_{N_2} \quad (43)$$

and update steps are as follows:

$$\gamma_0^{(j+1)} = \gamma_0^{(j)} - (u_0^{(j+1)} - Sx^{(j+1)}) \quad (44)$$

$$\gamma_1^{(j+1)} = \gamma_1^{(j)} - [u_1^{(j+1)} - (Dd_I - DSu_2^{(j+1)} - DSu_2^{(j+1)}) + Dd_I] \quad (45)$$

$$\gamma_2^{(j+1)} = \gamma_2^{(j)} - (u_2^{(j+1)} - x^{(j+1)}) \quad (46)$$

In Equation (39), computing inverse of $H_{v_1 v_2}$ can be impractical for large image sizes, so a preconditioned conjugate gradients method can be used for calculating $u_2$.

The minimization formulation in the reconstruction problem presented in Model 2 is similar to the Model 1 optimization model, but $u_1$ is defined differently based on $E_2$ in Equation (20).

$$\underset{x, u_0, u_1, u_2}{\operatorname{minimize}} g_0(u_0, u_1) \text{ subject to} \quad (47)$$

$$u_0 = Sx, \quad u_1 = D_2 d_I - D_2 Su_2 - 2DSDu_2 - SD_2 u_2, \quad u_2 = x$$

With the same matrices u, C, G, and B, and the same cost function except in B, parameter $L_2$ is defined as $D_2 S + 2DSD + SD_2$ and in matrix b, $Dd_I$ is replaced by $D_2 d_I$. Subproblems in Equations (32-35) can be defined as:

$$u_0^{(j+1)} = \underset{u_0}{\operatorname{argmin}} \frac{1}{2}\|d - Fu_0\|_2^2 + \frac{\mu}{2}\|u_0 - Sx^{(j)} - \gamma_0^{(j)}\|_2^2 \quad (48)$$

$$u_1^{(j+1)} = \underset{u_1}{\operatorname{argmin}} \beta\|D_2 d_I - D_2 Su_2^{(j)} - 2DSDu_2^{(j)} - SD_2 u_2^{(j)}\|_p + \quad (49)$$
$$\frac{\mu v_1}{2}\|u_1 - (D_2 d_I - D_2 Su_2^{(j)} - 2DSDu_2^{(j)} - SD_2 u_2^{(j)}) - \gamma_1^{(j)}\|_2^2$$

$$u_2^{(j+1)} = \quad (50)$$
$$\underset{u_2}{\operatorname{argmin}} \frac{\mu v_1}{2}\|u_1^{(j+1)} - (D_2 d_I - D_2 Su_2 - 2DSDu_2 - SD_2 u_2) - \gamma_1^{(j)}\|_2^2 +$$
$$\frac{\mu v_2}{2}\|u_2 - x^{(j)} - \gamma_2^{(j)}\|_2^2$$

$$x^{(j+1)} = \underset{x}{\operatorname{argmin}} \frac{\mu}{2}\|u_0^{(j+1)} - Sx - \gamma_0^{(j)}\|_2^2 + \frac{\mu v_2}{2}\|u_2^{(j+1)} - x^{(j)} - \gamma_2^{(j)}\|_2^2 \quad (51)$$

The solution for minimization in Equation (49) with respect to $u_1$ is similar to Equation (33) and solved based on the shrinkage rule in Equation (36). The minimization solutions for (48), (50), and (51) are as follows:

$$u_0^{(j+1)} = H_\mu^{-1}[F^H d + \mu(Sx^{(j)} + \gamma_0^{(j)})] \quad (52)$$

$$u_2^{(j+1)} = H_{v_1 v_2}^{-1}[v_1(S^H D_2^H + 2D^H S^H D^H + D_2^H S^H)(D_2 d_I - u_1^{(j+1)} + \gamma_1^{(j)}) + v_2(x^{(j)} + \gamma_2^{(j)})] \quad (53)$$

$$x^{(j+1)} = H_{v_2}^{-1}[S^H(u_0^{(j+1)} - \gamma_0^{(j)}) + v_2(u_2^{(j+1)} - \gamma_2^{(j)})] \quad (54)$$

where $$H_\mu = F^H F + \mu I_{N_1} \quad (55)$$

$$H_{v_1 v_2} = v_1(S^H D_2^H D_2 S + 2S^H D_2^H DSD + S^H D_2^H SD_2 + 2D^H S^H D^H D_2 S + 4D^H S^H D^H DSD + 2D^H S^H D^H SD_2 + D_2^H S^H D_2 S + 2D_2^H S^H DSD + D_2^H S^H SD_2) + v_2 I_{N_2} \quad (56)$$

$$H_{v_2} = S^H S + v_2 I_{N_2} \quad (57)$$

Similar to Equation (39), $u_2$ in Equation (53) can be computed through a few iterations of a preconditioned conjugate gradients method. The update steps can be as follows:

$$\gamma_0^{(j+1)} = \gamma_0^{(j)} - (u_0^{(j+1)} - Sx^{(j+1)}) \quad (58)$$

$$\gamma_1^{(j+1)} = \gamma_1^{(j)} - [u_1^{(j+1)} - (D_2 d_I - D_2 Su_2^{(j+1)} - 2DSDu_2^{(j+1)} - SD_2 u_2^{(j+1)}) + D_2 d_I] \quad (59)$$

$$\gamma_2^{(j+1)} = \gamma_2^{(j)} - (u_2^{(j+1)} - x^{(j+1)}) \quad (60)$$

The reconstruction problem presented in Model 3 can be defined by minimizing the same cost criterion as in Model 1 and Model 2 with both constraints included:

$$\underset{x, u_0, u_1, u_2, u_3}{\text{minimize}} \; g_0(u_0, u_1, u_2) \text{ subject to} \quad (61)$$

$$u_0 = Sx, \; u_1 = Dd_I - DSu_3 - SDu_3,$$
$$u_2 = D_2 d_I - D_2 Su_3 - 2DSDu_3 - SD_2 u_3, \; u_3 = x$$

where $$g(u_0, u_1, u_2) = \frac{1}{2}\|d - Fu_0\|_2^2 + \beta_1 \|u_1\|_p + \beta_2 \|u_2\|_p \quad (62)$$

The minimization problem can be rewritten using the general Augmented Lagrangian framework defined in Equation (23) as:

$$u = \begin{bmatrix} u_0 \\ u_1 \\ u_2 \\ u_3 \\ x \end{bmatrix} \quad (63)$$

$$g(u) = g(u_0, u_1, u_2), \; C = GB, \; b = \begin{bmatrix} 0 \\ Dd_I \\ D_2 d_I \\ 0 \end{bmatrix} \quad (64)$$

$$G = \begin{bmatrix} I_{N_1} & 0 & 0 & 0 \\ 0 & \sqrt{v_1} I_D & 0 & 0 \\ 0 & 0 & \sqrt{v_2} I_{N_2} & 0 \\ 0 & 0 & 0 & \sqrt{v_3} I_{N_3} \end{bmatrix} \quad (65)$$

$$B = \begin{bmatrix} I_{N_1} & 0 & 0 & 0 & -S \\ 0 & I_D & 0 & L_2 & 0 \\ 0 & 0 & I_{N_2} & L_3 & 0 \\ 0 & 0 & 0 & I_{N_3} & -I_{N_3} \end{bmatrix} \quad (66)$$

where $L_2 = SD + DS$ and $L_3 = D_2 S + 2DSD + SD_2$ and $v_{1,2,3} > 0$. The Augmented Lagrangian function can be defined by:

$$\mathcal{L}(u, \gamma, \mu) = g(u_0, u_1, u_2) + \frac{\mu}{2}\|Bu - \gamma\|_2^2 \text{ where} \quad (67)$$

$$\gamma = b - \left(\frac{1}{\mu}\right) G^{-1}\alpha \text{ and } \alpha = [\alpha_0^H \; \alpha_1^H \; \alpha_2^H \; \alpha_3^H]^H.$$

By applying the alternating minimization method to Equation (67), the following subproblems can be produced:

$$u_0^{(j+1)} = \underset{u_0}{\operatorname{argmin}} \frac{1}{2}\|d - Fu_0\|_2^2 + \frac{\mu}{2}\|u_0 - Sx^{(j)} - \gamma_0^{(j)}\|_2^2 \quad (68)$$

$$u_1^{(j+1)} = \underset{u_1}{\operatorname{argmin}} \beta_1 \|Dd_I - DSu_3^{(j)} - SDu_3^{(j)}\|_p + \frac{\mu v_1}{2}\|u_1 - (Dd_I - DSu_3^{(j)} - SDu_3^{(j)}) - \gamma_1^{(j)}\|_2^2 \quad (69)$$

$$u_2^{(j+1)} = \underset{u_2}{\operatorname{argmin}} \beta_2 \|D_2 d_I - D_2 Su_3^{(j)} - 2DSDu_3^{(j)} + SD_2 u_3^{(j)}\|_p + \frac{\mu v_2}{2}\|u_2 - (D_2 d_I - D_2 Su_3^{(j)} - 2DSDu_3^{(j)} - SD_2 u_3^{(j)}) - \gamma_2^{(j)}\|_2^2 \quad (70)$$

$$u_3^{(j+1)} = \underset{u_3}{\operatorname{argmin}} \frac{\mu v_1}{2}\|u_1^{(j+1)} - (Dd_I - DSu_3 - SDu_3) - \gamma_1^{(j)}\|_2^2 + \frac{\mu v_2}{2}\|u_2^{(j+1)} - (D_2 d_I - D_2 Su_3 - 2DSDu_3 - SD_2 u_3) - \gamma_2^{(j)}\|_2^2 + \frac{\mu v_3}{2}\|u_3 - x^{(j)} - \gamma_3^{(j)}\|_2^2 \quad (71)$$

$$x^{(j+1)} = \underset{x}{\operatorname{argmin}} \frac{\mu}{2}\|u_0^{(j+1)} - Sx - \gamma_0^{(j)}\|_2^2 + \frac{\mu v_3}{2}\|u_3^{(j+1)} - x - \gamma_3^{(j)}\|_2^2 \quad (72)$$

The solution for minimization in equations (69), (70) with respect to $u_1$ and $u_2$ respectively, are similar to Equation (33) and can be solved based on the shrinkage rule in Equation (36). The minimization solutions for (68), (71), and (72) are as follows:

$$u_0^{(j+1)} = H_\mu^{-1}\left[F^H d + \mu\left(Sx^{(j)} + \gamma_0^{(j)}\right)\right] \quad (73)$$

$$u_3^{(j+1)} = H_{v_1 v_2 v_3}^{-1}\left[v_1(D^H S^H + S^H D^H)(Dd_I - u_1^{(j+1)} + \gamma_1^{(j)}) + v_2(S^H D_2^H + 2D^H S^H D^H + D_2^H S^H)(D_2 d_I - u_2^{(j+1)} + \gamma_2^{(j)}) + v_3(x^{(j)} + \gamma_3^{(j)})\right] \quad (74)$$

$$x^{(j+1)} = H_{v_3}^{-1}\left[S^H\left(u_0^{(j+1)} - \gamma_0^{(j)}\right) + v_3\left(u_3^{(j+1)} - \gamma_3^{(j)}\right)\right] \quad (75)$$

where $$H_\mu = F^H F + \mu I_{N_1} \quad (76)$$

-continued $$H_{v_1v_2v_3} = v_1(D^H S^H DS + D^H S^H SD + S^H D^H DS + S^H D^H SD) + \quad (77)$$
$$v_2(S^H D_2^H D_2 S + 2S^H D_2^H DSD + S^H D_2^H SD_2 +$$
$$2D^H S^H D^H D_2 S + 4D^H S^H D^H DSD + 2D^H S^H D^H SD_2 +$$
$$D_2^H S^H D_2 S + 2D_2^H S^H DSD + D_2^H S^H SD_2) + v_3 I_{N_3}$$

$$H_{v_3} = S^H S + v_3 I_{N_3} \quad (78)$$

and update steps are as follows:

$$\gamma_0^{(j+1)} = \gamma_0^{(j)} - (u_0^{(j+1)} - Sx^{(j+1)}) \quad (79)$$

$$\gamma_1^{(j+1)} = \gamma_1^{(j)} - [u_1^{(j+1)} - (Dd_f - DSu_3^{(j+1)} - SDu_3^{(j+1)}) + Dd_f] \quad (80)$$

$$\gamma_2^{(j+1)} = \gamma_2^{(j)} - [u_2^{(j+1)} - (D_2 d_f - D_2 Su_3^{(j+1)} - 2DSDu_3^{(j+1)} - SD_2 u_3^{(j+1)} - SD_2 u_3^{(j+1)}) + D_2 d_f] \quad (81)$$

$$\gamma_3^{(j+1)} = \gamma_3^{(j)} - (u_3^{(j+1)} - x^{(j+1)}) \quad (82)$$

Similar to the previous models, the computation of $u_2$ in Equation (77) can be done through a few iterations of a preconditioned conjugate gradients method.

FIGS. 4 through 11 illustrate results obtained through implementation of the reconstruction methods described here. The present reconstruction methods can outperform other known reconstruction methods, such as Generalized Autocalibrating Partial Parallel Acquisition (GRAPPA) reconstruction, across different acceleration rates. The equality constraints improve the conditioning of the system equations, which reduces the geometry factor artifact and provides higher image quality even at high acceleration factors.

The reconstruction methods have been implemented in MATLAB (Mathworks, Natick, Massachusetts). In general, the methods can be applied to data with different dimensions, including 2D, 3D, and 4D. However, only the results corresponding to 2D and 3D data are reported here. In addition to the encoding matrix E, the finite difference operators can be different for a 3D implementation compared to a 2D implementation. For example, in 3D data, D and $D_2$ can be defined as first and second-order finite difference operators in three different directions (as opposed to two directions in 2D).

The implementation can include four steps: (1) an initialization step, (2) a pre-computation step in which the fixed terms that are constant across different iterations are pre-computed, (3) a subproblems solution step, and (4) an update step. The values for parameters $\mu$, $v_1$, $v_2$, and/or $v_3$ can influence the overall convergence rate in some implementations of the reconstruction method. In some implementations, the results and convergence rate can be optimized by setting $\mu$ so that the condition number(s) of are bounded. In some implementations, the values for $v_1$, $v_2$, and/or $v_3$ (in a Model 3 solution) can be found empirically, as discussed below.

To emphasize the generality and flexibility of the reconstruction methods described here, the performance of the methods are evaluated on three different undersampled datasets with different pulse sequences and different number of receiver channels. For all three datasets, fully sampled k-space data reconstructed using the adaptive combine method is used as a standard for comparison. A standard method of undersampling is used: in 2D datasets, even lines are acquired in the phase encoding direction, whereas in 3D datasets, undersampling was applied in both phase encoding directions. The coil sensitivity profiles were computed using the ESPIRiT method applied to a 24×24×24 and 32×32 Cartesian grid of calibration data for 3D and 2D data, respectively, although various other methods can be used.

The three data sets appearing in the reported results were acquired using 3D Magnetization Prepared Rapid Gradient Echo (MPRAGE), 3D Gradient Echo (GRE), and 2D T2 Fast Spin Echo (FSE). A Siemens PRISMA scanner (Siemens, Munich, Germany) was used with a 64-channel head and neck coil for the T2 FSE and 3D GRE experiments. A Siemens TRIO scanner (Siemens, Munich, Germany) with a 32-channel head coil was used for the 3D MPRAGE scans.

For the 2D T2 FSE Acquisition, the echo time (TE) of the scan was 89 ms with a repetition time (TR) of 11.3 s. The FOV was 230×186 mm$^2$ with a matrix size of 512×416, resulting in an in-place resolution of 0.45 mm. Sixty (60) slice were acquired with a slice thickness of 2.5 mm. Total scan time for the full k-space acquisition was 4 minutes and 43 seconds. Bandwidth per pixel was set at 200 Hz/pixel.

For the 3D MPRAGE acquisition, the echo time (TE) of the scan was 2.17 ms with a repetition time (TR) of 1.56 s. The field of view was 256×256×176 mm$^3$ with a matrix size of 256×256×176, resulting in an isotropic 1 mm resolution. Inversion time was 900 ms. Each volunteer was scanned multiple times.

For the 3D GRE acquisition, the echo time (TE) of the scan was 3.45 ms with a repetition time (TR) of 8 ms. The field of view was 256×256×192 mm$^3$ with a matrix size of 256×256×192, resulting in an isotropic 1 mm resolution. Flip angle was set as 25 degrees and bandwidth per pixel was 200 Hz/pixel. Scan time for full k-space acquisition was 6 minutes and 33 seconds. Different in plane and slice acceleration factors were acquired in a volunteer study. For 2× in plane and 2× slice acceleration the scan time was 100 seconds. For 4× in plane and 4× slice acceleration the scan time was 28 seconds.

Each dataset was reconstructed using the methods described here and the GRAPPA method, which considered a reliable and standard method in different MRI scanners. Different kernel sizes were used with Tikhonov regularization for the kernel calibration. Different GRAPPA kernel sizes were considered, and the best results were chosen for comparison.

If the equality constraints in the reconstruction methods described here are enforced by extending the encoding matrices, then the geometry factor can be defined as:

$$g_i = \sqrt{((E^H E)^{-1})_{ii}(E^H E)_{ii}} \quad (83)$$

Since the extended encoding matrices E, $E^H$, and $E^H E$ require large amounts of memory, geometry factor maps can be computed using Monte-Carlo simulations. In Monte-Carlo simulations, noise maps are acquired by repeatedly corrupting the k-space data with properly scaled and correlated synthetic noise.

Figure 4:
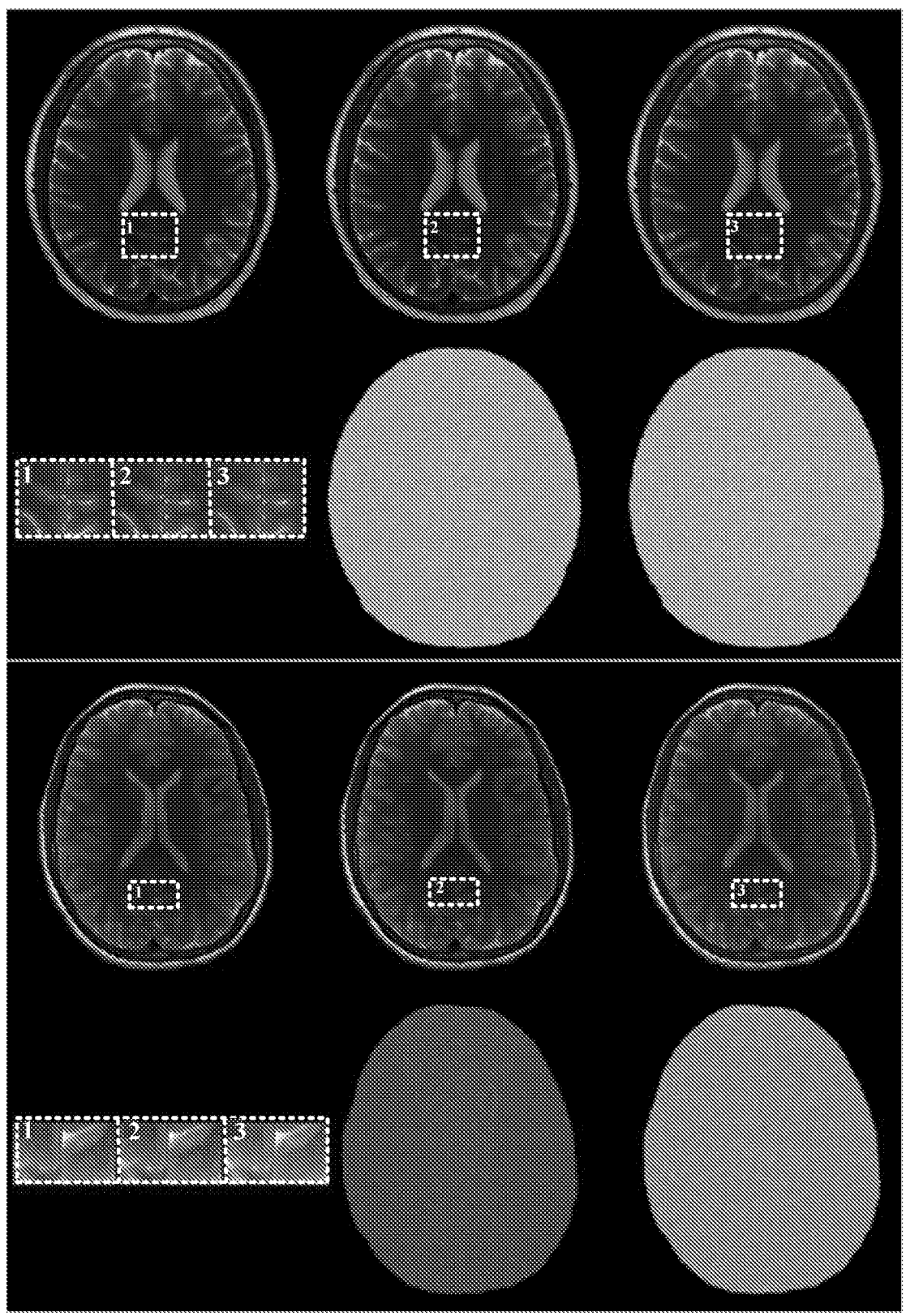
FIGS. 4 through 8 are comparisons of reconstructed images using different image reconstruction methods.
Figure 5:
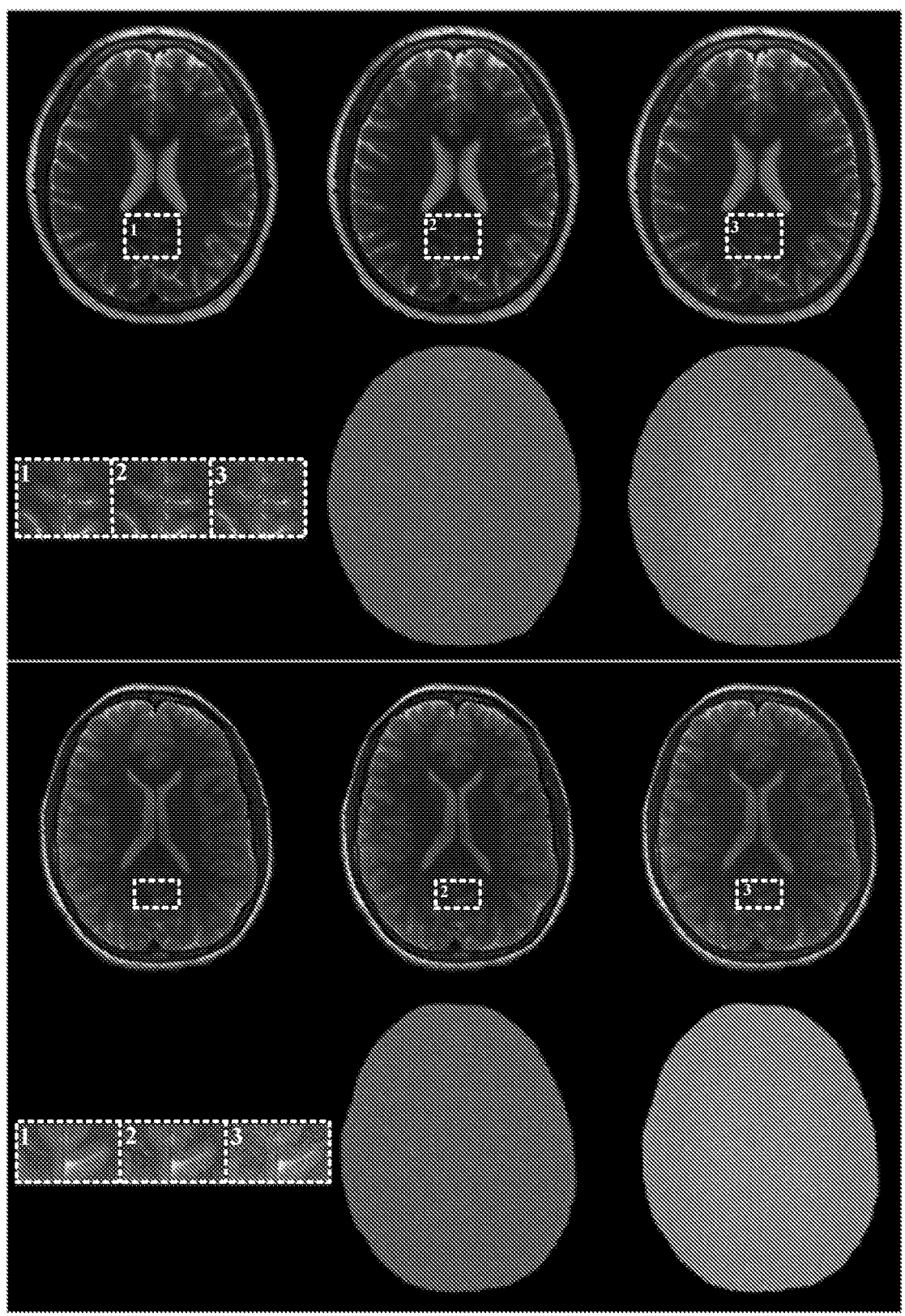

Results:

FIGS. 4 and 5 are comparisons of MRI reconstructions for the 2D T2 datasets using the reconstruction method presented in Model 1 and the GRAPPA method for undersampling factors of 2 and 4. The first row (from left to right) shows the gold standard reconstruction result using fully sampled data, the reconstruction result using the method presented in Model 1 with an undersampling factor of 2, and the GRAPPA reconstruction result with an undersampling factor of 2 for 2D T2 FSE data. The second row (from left to right) shows a magnification of selected areas of each reconstruction, and error maps corresponding to each of the reconstruction results. As shown in FIG. 4, with an undersampling factor of 2, the reconstruction method described here reconstructs artifact-free images that have slightly better quality than the images reconstructed with GRAPPA. However, GRAPPA also performs well in this case, which is considered a low acceleration factor and for which we have well-conditioned inverse problem.

FIG. 5 shows a similar comparison as shown in FIG. 4, but with undersampling factor of 4 which is considered a high acceleration factor. The first row (from left to right) shows the gold standard reconstruction result using fully sampled data, the reconstruction result using the method presented in Model 1 with undersampling factor of 4, and the GRAPPA reconstruction result with undersampling factor of 4 for 2D T2 FSE data. The second row (from left to right) shows a magnification of selected areas of each reconstruction, and error maps corresponding to each of the reconstruction results. For high acceleration (i.e., an undersampling factor of 4), GRAPPA shows more severe artifacts and noise amplification compared to the reconstruction method described here.

Figure 6:
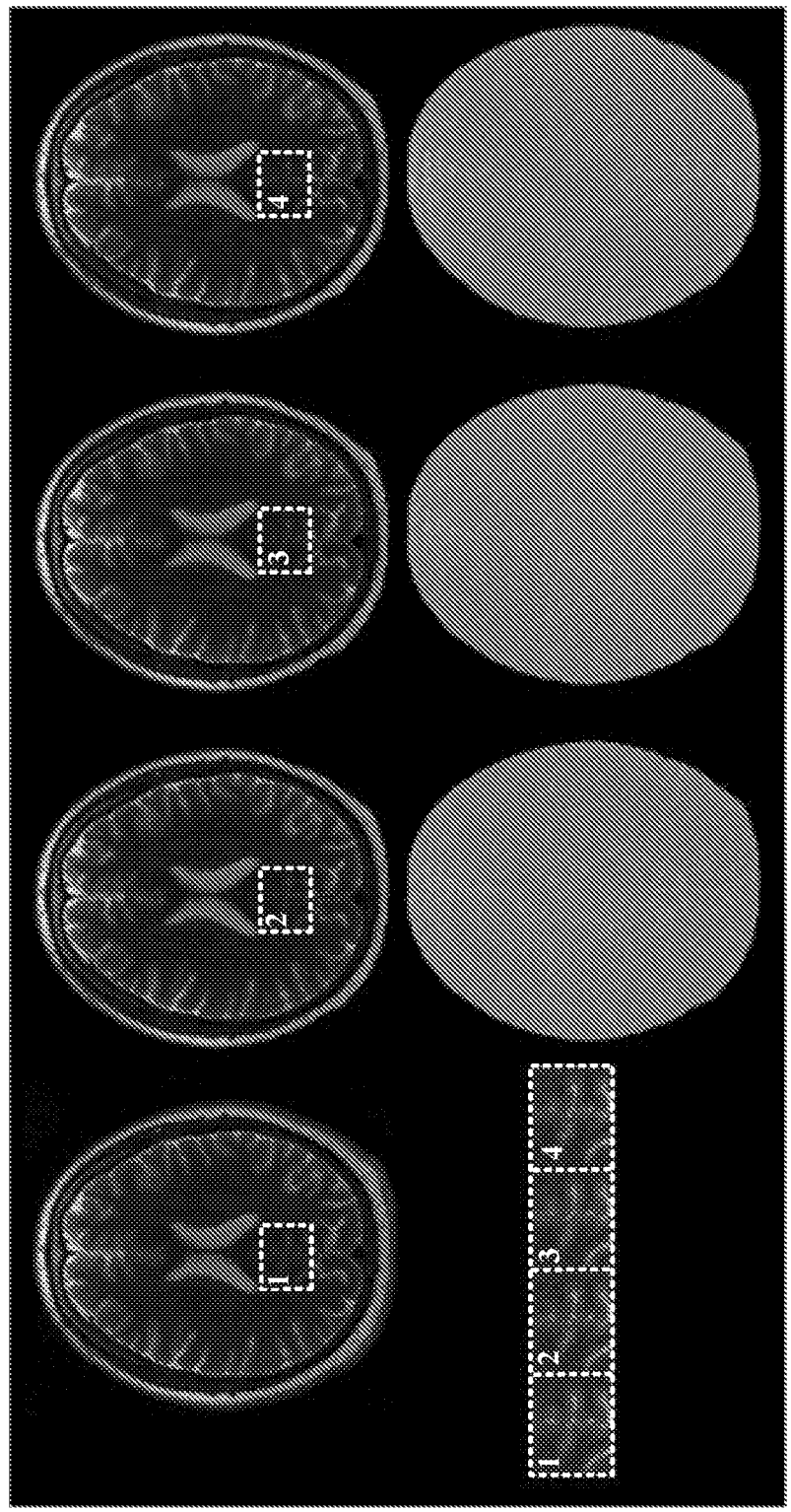

FIG. 6 shows a comparison between the three different formulations of the reconstruction equations described in Models 1, 2, and 3 for 2D T2 data. The first row (from left to right) shows the gold standard reconstruction result using fully sampled data, the reconstruction result using the Model 1 formulation with an undersampling factor of 4, the reconstruction result using the Model 2 formulation with an undersampling factor of 4, and the reconstruction result using the Model 3 formulation with an undersampling factor of 4 for 2D T2 FSE data. The second row (from left to right) shows a magnification of selected areas of each reconstruction, and error maps corresponding to each of the reconstruction results. The normalized root-mean-square errors (NRMSE) that correspond to the Model 1, 2, and 3 reconstruction formulations are 0.0121, 0.0137, and 0.0119, respectively. The Model 1 reconstruction (Equation (19)) which incorporates first-order gradient constraint in the reconstruction framework performs better when compared to the Model 2 reconstruction (Equation (20)). This result can be due to a decrease in signal information that is preserved when only a second-order gradient constraint of sensitivities is used. The Model 3 reconstruction (Equation (21)) which exploits the advantages of both models provides slightly better results when compared to the Model 1 reconstruction. However, the Model 3 reconstruction is more computationally expensive than the Model 1 reconstruction.

Figure 7A:
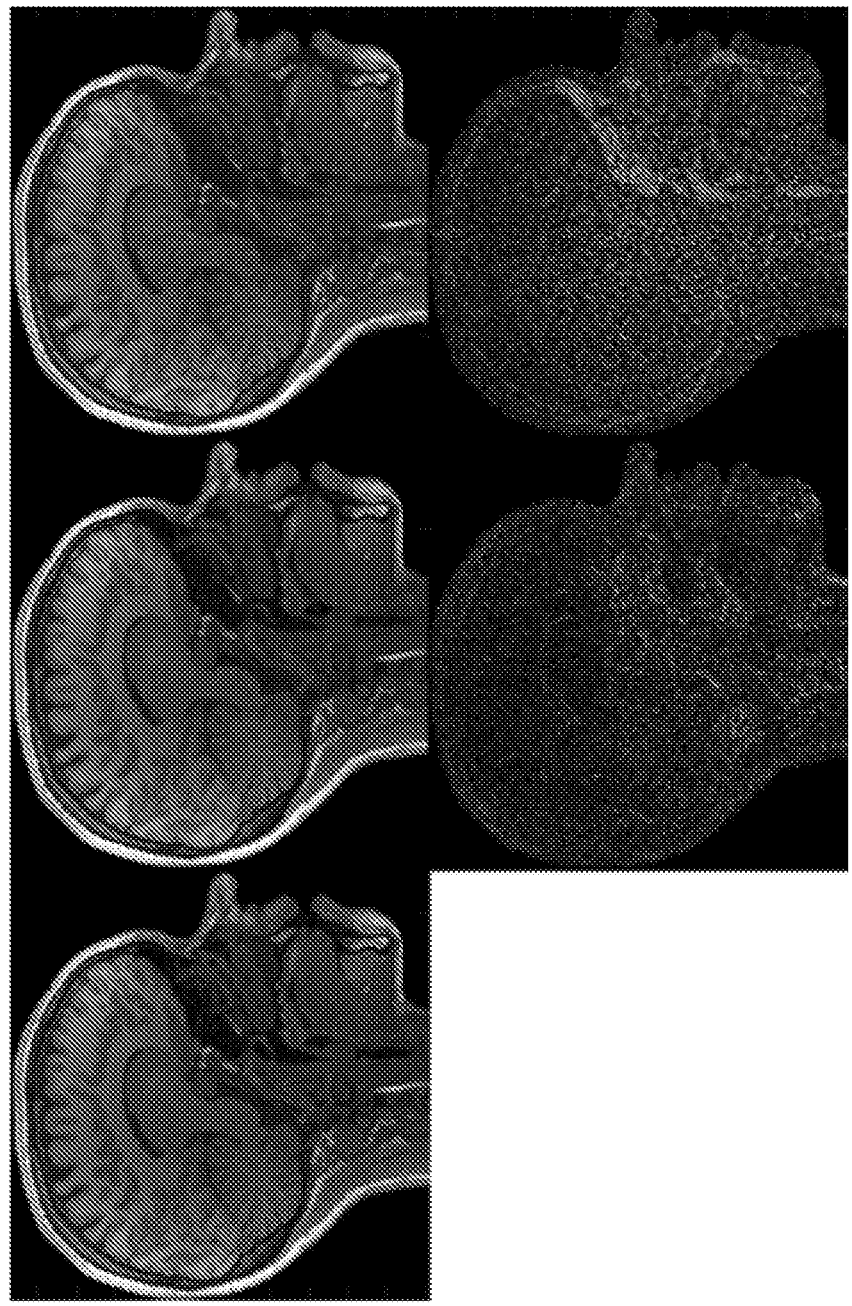

FIG. 7a shows a comparison of MRI reconstructions for the 3D MPRAGE datasets of using the reconstruction method presented in Model 1 and the GRAPPA method with an undersampling factor of 4×1. The first row (from left to right) shows the gold standard reconstruction result using fully sampled data, the reconstruction result using the method presented in Model 1 with an undersampling factor of 4×1 along one phase encoding dimension, and the GRAPPA reconstruction result with an undersampling factor of 4×1 along one phase encoding dimension for 3D MPRAGE data. The second row (from left to right) shows error maps corresponding to each of the reconstruction results.

Figure 7B:
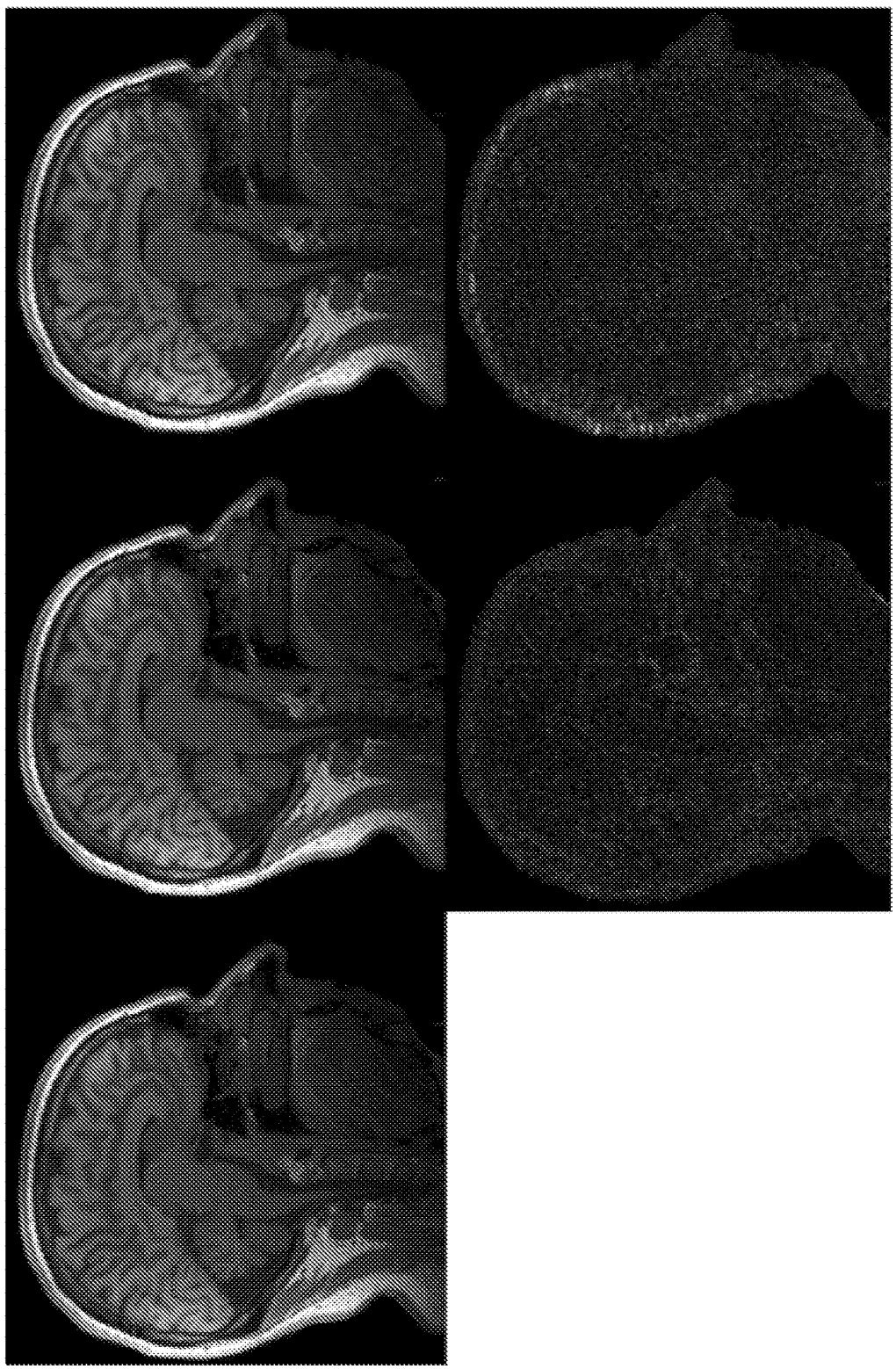

FIG. 7b shows a comparison of MRI reconstructions for the 3D MPRAGE datasets of using the reconstruction method presented in Model 1 and the GRAPPA method with an undersampling factor of 2×2. The first row (from left to right) shows the gold standard reconstruction result using fully sampled data, the reconstruction result using the method presented in Model 1 with an undersampling factor of 2×2 along both phase encoding dimensions, and the GRAPPA reconstruction result with an undersampling factor of 2×2 along both phase encoding dimensions for 3D MPRAGE data. The second row (from left to right) shows error maps corresponding to each of the reconstruction results.

Figure 8:
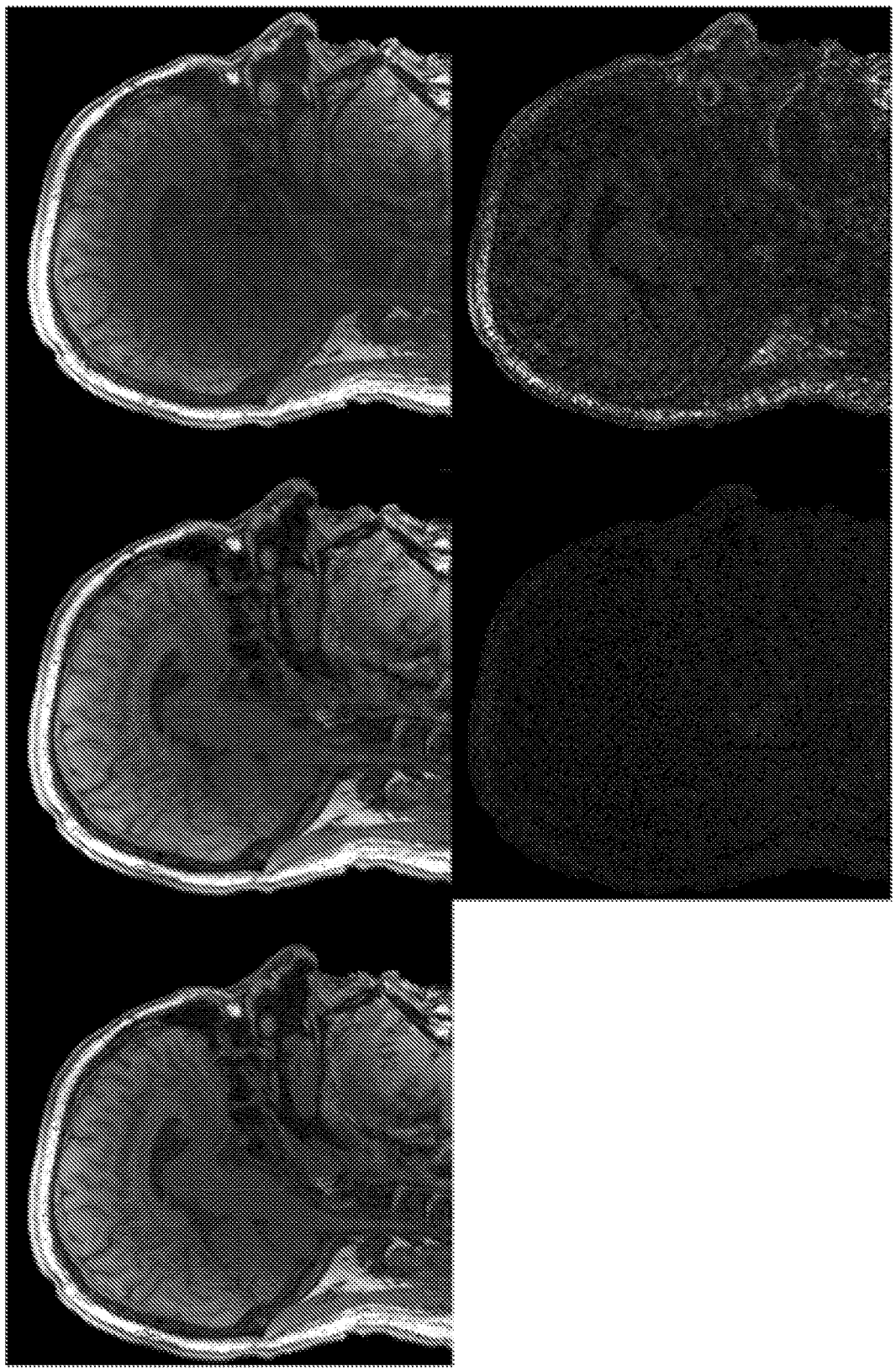

FIG. 8 shows a comparison of MRI reconstructions for the 3D GRE datasets of using the reconstruction method presented in Model 1 and the GRAPPA method with an undersampling factor of 2×2. The first row (from left to right) shows the gold standard reconstruction result using fully sampled data, the reconstruction result using the method presented in Model 1 with an undersampling factor of 2×2 along both phase encoding dimensions, and the GRAPPA reconstruction result with an undersampling factor of 2×2 along both phase encoding dimensions for 3D MPRAGE data. The second row (from left to right) shows error maps corresponding to each of the reconstruction results.

Figure 9:
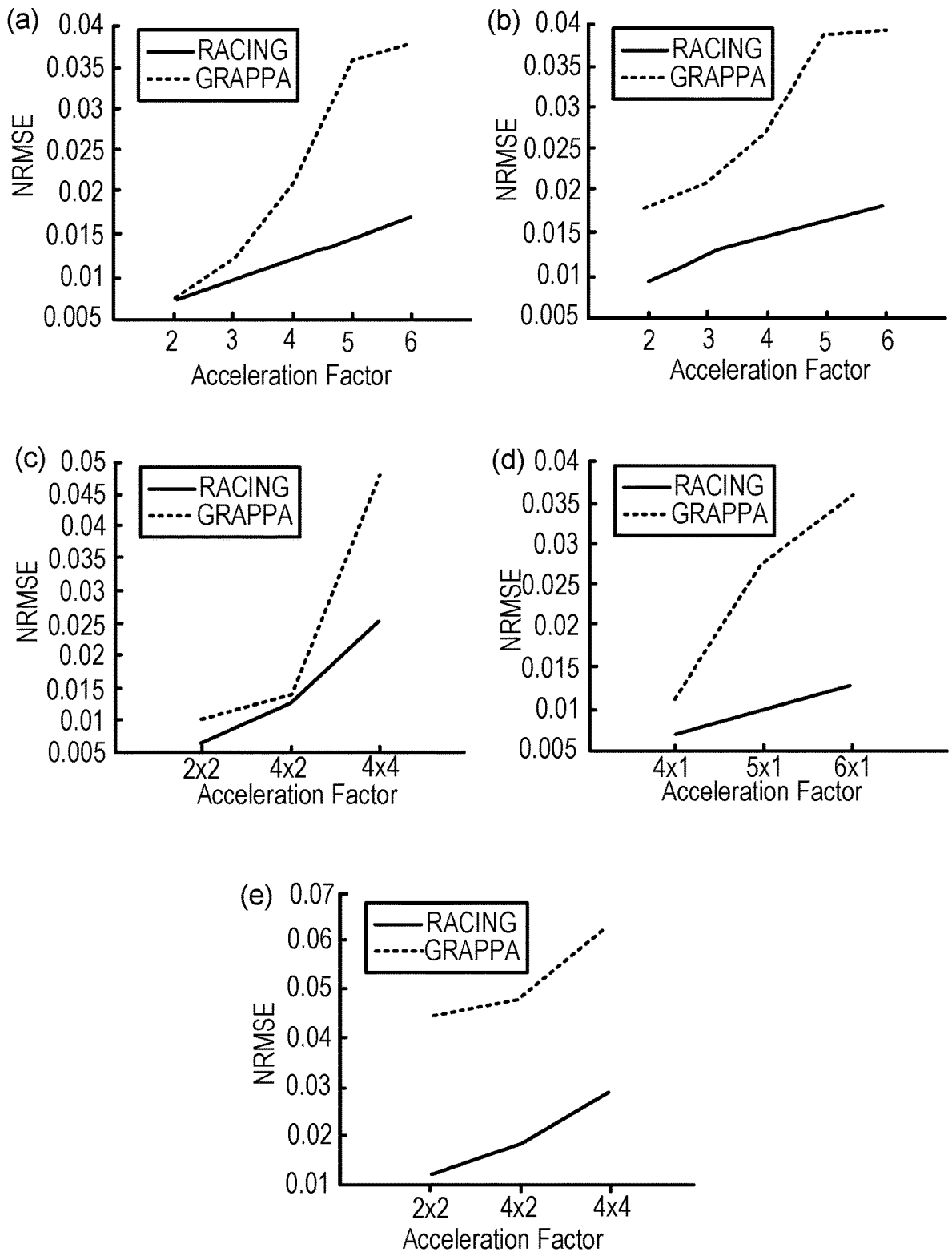
FIG. 9 is series of graphs of the normalized root-mean-square errors of reconstructed images.

FIG. 9 shows plots of NRMSE values of the experiments for different acceleration factors using 2D T2 data (plots (a) and (b) (first and second volunteers respectively)), 3D MPRAGE data (plots (c) and (d) (third and second volunteers respectively)), and 3D GRE data (plot (e) (first volunteer)). As expected, the reconstruction accuracy reduces rapidly for GRAPPA reconstruction as the acceleration factor increases. Overall, the reconstruction method described here provides a dramatic improvement over GRAPPA as the acceleration factor increases in all cases.

Figure 10:
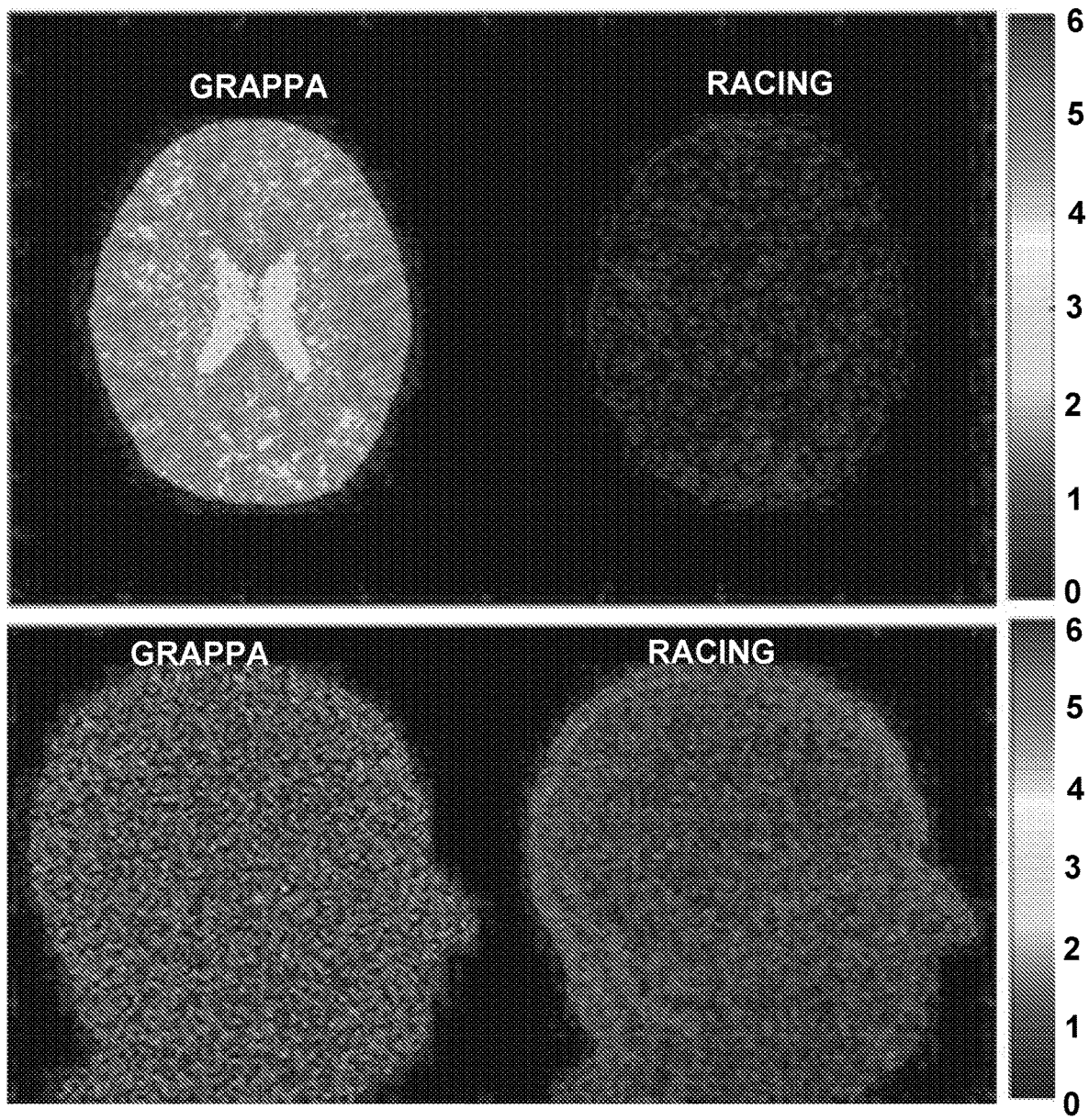
FIG. 10 is a map of geometry factor artifacts.

FIG. 10 shows the geometry factor maps for undersampled 2D T2 FSE data (first volunteer with undersampling factor of 4), and undersampled 3D MPRAGE data (third volunteer with undersampling factor of 2×2), obtained through MonteCarlo simulations. For 2D data, the mean geometry factor values computed using GRAPPA and the method described here are 1.69 and 0.39, respectively. For 3D data, the mean geometry factor values computed using GRAPPA and the method described here are 2.45 and 0.64, respectively.

Figure 11:
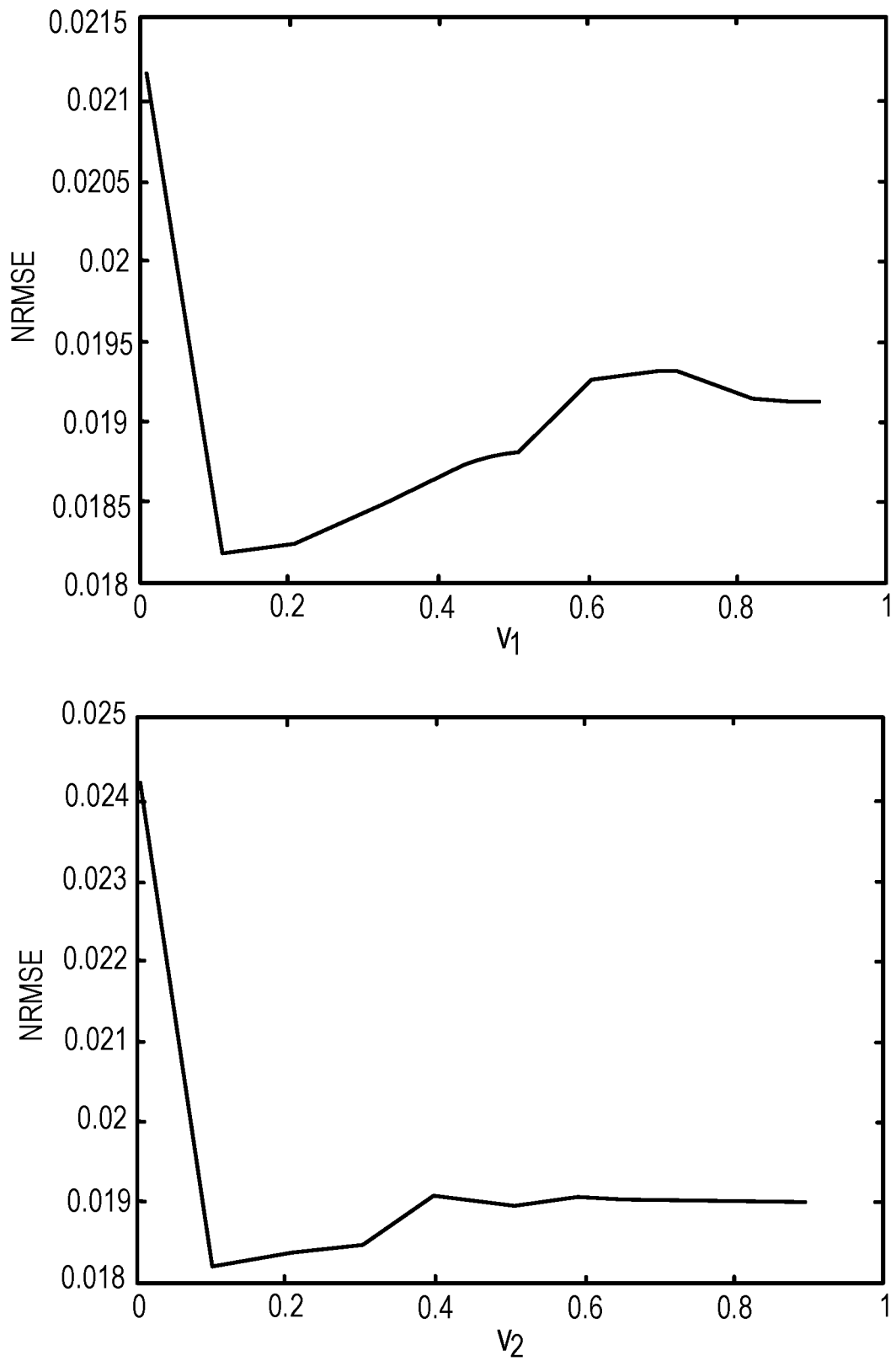
FIG. 11 is a series of graphs of the normalized root-mean-square errors of reconstruction parameters.

FIG. 11 shows plots of the reconstruction performance in terms of parameters $v_1$ (top) and $v_2$ (bottom) for undersampled 2D T2 FSE data (with undersampling factor of 4 and a fixed number of iterations). Other parameters are considered fixed in both plots. As shown, the reconstruction NRMSE is relatively stable across a wide range of $v_1$ and $v_2$ values. Thus, parameter fine-tuning may not be necessary in across different reconstruction scenarios.

As shown in the results reported in FIGS. 4 through 11, the reconstruction method described here can outperform GRAPPA reconstruction with different acceleration rates. The equality constraints improve the conditioning of the system equations, which reduces the geometry factor artifact and provides higher image quality even at high acceleration factors.

Various modifications to the reconstruction methods described here are possible. For instance, a k-space implementation of the reconstruction method is possible by, for example, taking a Fourier transform of the image space least squares solution equation. This turns the matrix multiplication into a convolution, and the optimal k-space reconstruction kernel can be the best approximation to the Fourier transform of our image space reconstruction operator. Further, the reconstruction method can be applied to data acquired using conventional Cartesian, undersampled Cartesian, and non-cartesian k-space sampling strategies.

In the discussion above, equality constraint were computed based on spatial derivatives of the image formation equation. This has the intuitive advantage of exploiting differences in the orientation of the coil sensitivity profiles, but alternative constraints can also be constructed, such as finite difference derivative operators, derivatives of Gaussian filters, or other derivative operators. In some implementation, operators other than derivative operators can be used, such as low pass filters, high pass filters, steerable filters, or other operators, such as those that can couple the solution for a voxel to other, neighboring voxels.

In some implementations, the reconstruction method can be used in the presence of motion, in which case the MR signals can be related to one another via a spatial transformation. For instance, the image formation equation can include, for example, affine motion. In such a case, the image formed in one position can be identical to the same anatomy imaged in a second position, and the techniques described here can derive reconstruction constraints from such a relationship to improve the image quality.

In some implementations, the reconstruction method can include constraints that arise due to a relationship between images formed by one or more subsets of the receiver coils. For example, the reconstruction method can be used to reconstruct an image using MR signals detected by one or more subsets of the receiver coils. Because the same image is formed by each subset of the coils, additional constraints can be derived.

In some implementations, the reconstruction method can include constraints that arise from forming MR signals with multiple contrasts. For example, MRI can be T1 weighted or T2 weighted, among others, and can have each weighting to different degrees. Additional constraints for the reconstruction method can be derived by jointly reconstructing with different contrasts. Further, because MRI signal relaxation occurs over time, constraints can be derived to exploit the temporal dependence of the relaxation structure.

In some implementations, the constrained image reconstruction methods described here can be combined with other reconstruction strategies that allow acceleration, such as compressed sensing MRI, parallel MRI such as sensitivity encoding (SENSE) and GRAPPA and their generalizations, MRI fingerprinting, low rank constraints, controlled aliasing in parallel imaging (CAIPI) and wave-CAIPI reconstruction, among others.

Figure 12:
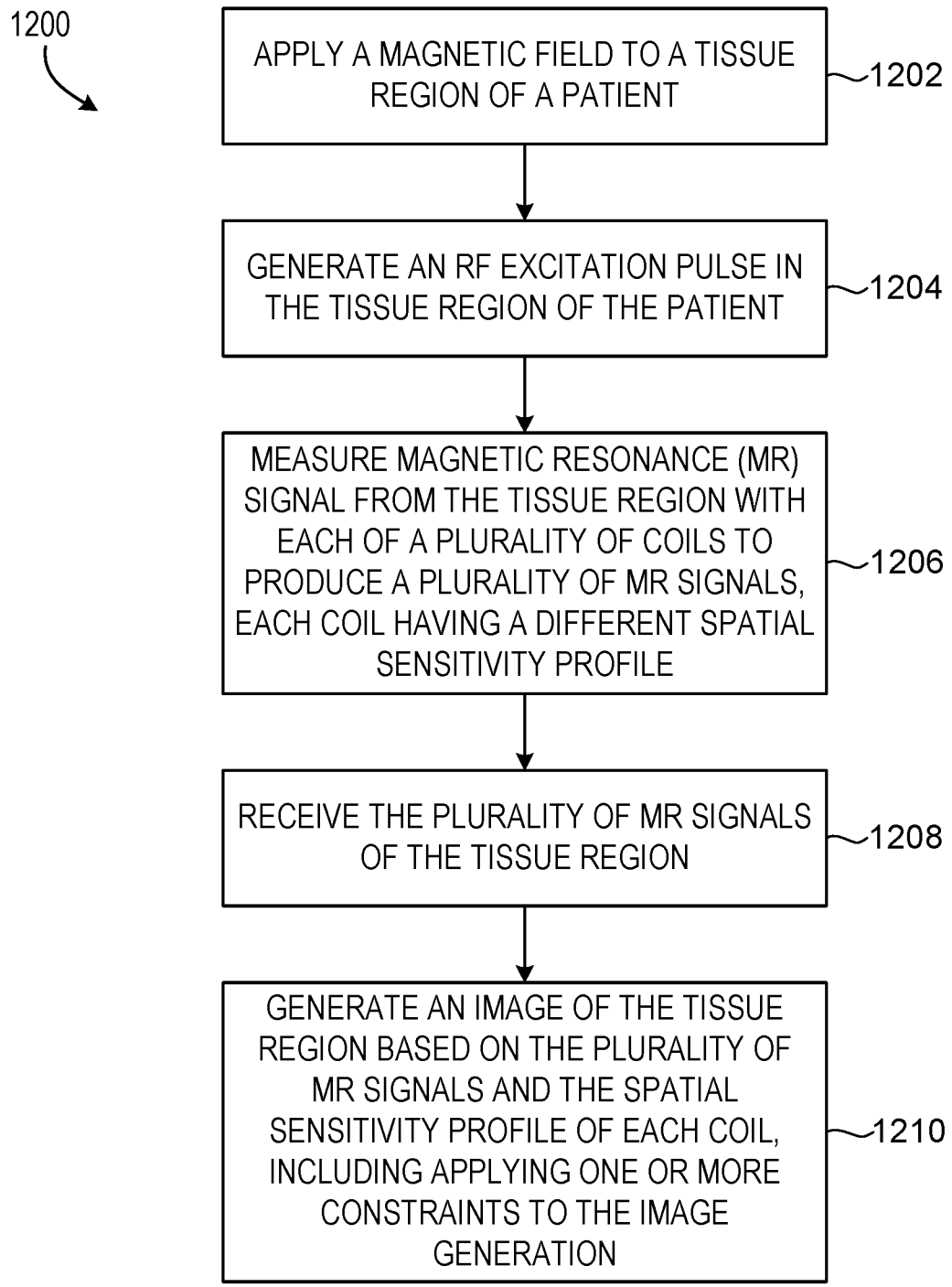
FIG. 12 is a flowchart of an example process for MRI reconstruction.

FIG. 12 is a flowchart of an example process 1200 for image reconstruction in accordance with the techniques described here. At least a portion of the process can be implemented using the MRI system 100. Operations of the process 1200 include applying a magnetic field to a tissue region of a patient (1202). The magnetic field can be applied by, for example, the main coil 120 or the gradient coils 124, or both. The process 1200 further includes generating an RF excitation pulse in the tissue region of the patient (1204). The RF excitation pulse can be generated by, for example, the RF transmitter 126 using some or all of the RF coils 130.

Operations of the process 1200 include measuring magnetic resonance (MR) signal from the tissue region with each of a plurality of coils to produce a plurality of MR signals, each coil having a different spatial sensitivity profile (1206). In some implementations, the tissue region can be measured with an acceleration factor greater than or equal to two. In some implementations, the tissue region can be measured in Cartesian space. In some implementations, the tissue region can be measured in non-Cartesian space.

Operations of the process 1200 include receiving the plurality of MR signals of the tissue region (1208) and generating an image of the tissue region based on the plurality of MR signals and the spatial sensitivity profile of each coil, including applying one or more constraints to the image generation (1210). At least one of the constraints can couple a first image value to one or more neighboring image values. In some implementations, the first image value is associated with a pixel or a voxel of the image. In some implementations, the first image value is spatially adjacent to the one or more other image values in the image. In some implementations, at least one of the constraints couples a value of a first image generated from MR signals measured by a first subset of the plurality of coils to a value of a second image generated from MR signals measured by a second subset of the plurality of coils, the first subset of coils being different than the second subset of coils.

Generating the image can include solving a system of equations subject to the one or more constraints. In some implementations, generating the image includes determining a least squares solution to the system of equations. In some implementations, generating the image includes determining an augmented Lagrangian solution to the system of equations.

Applying the one or more constraints can reduce the geometry factor of the image. In some implementations, the one or more constraints include equality constraints in the system of equations. In some implementations, applying the one or more constraints includes applying a spatial derivative to the plurality of MR signals and the spatial sensitivity profile of each coil. In some implementations, applying the one or more constraints includes applying a filter to the plurality of MR signals and the spatial sensitivity profile of each coil. In some implementations, applying the one or more constraints includes applying a spatial transformation to the plurality of MR signals. In some implementations, applying the one or more constraints includes relating a first MR signal associated with a first contrast to a second MR signal associated with a second contrast.

Figure 13:
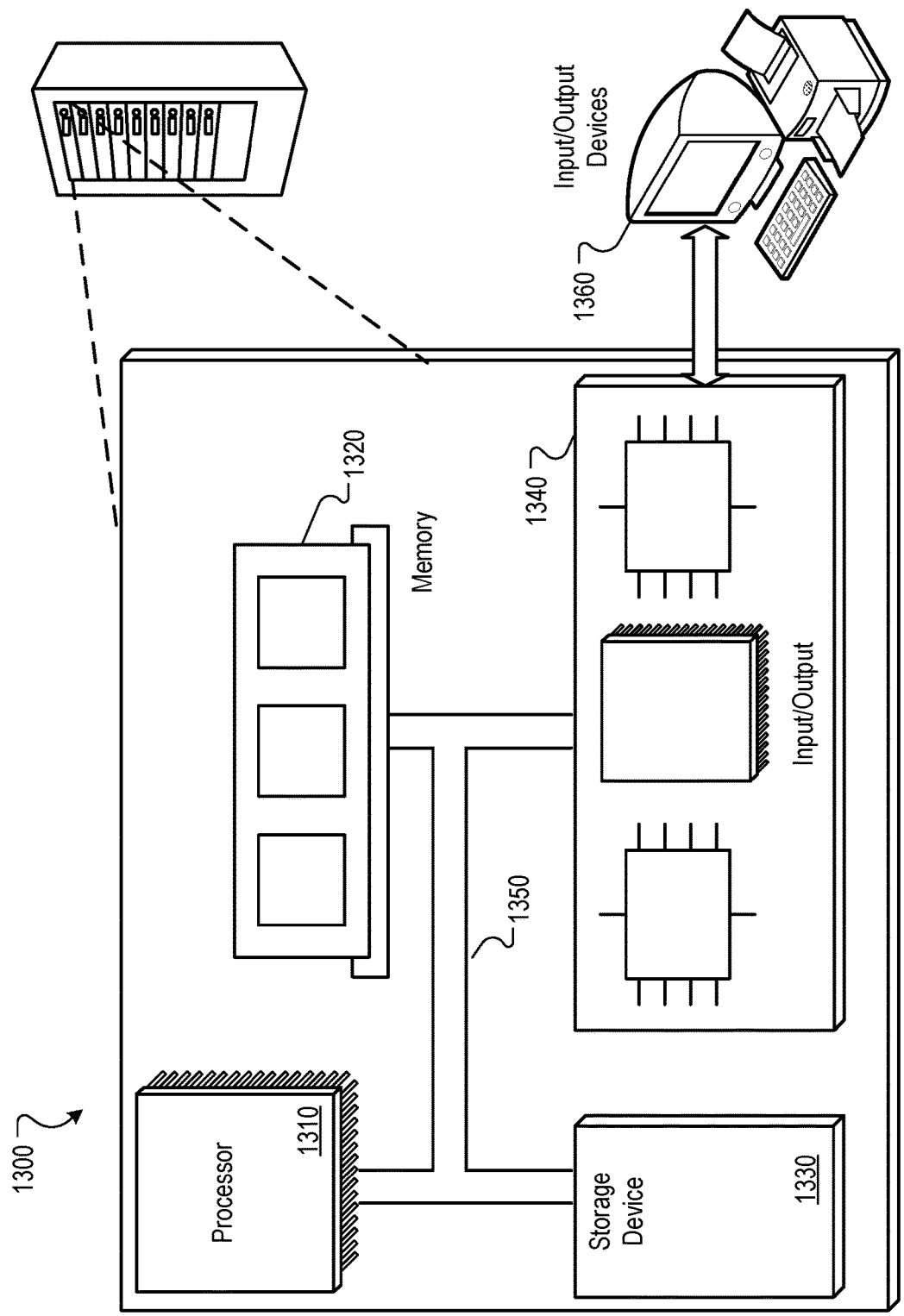
FIG. 13 is a schematic diagram of a computer system.

FIG. 13 is a block diagram of an example computer system 1300. For example, referring to FIG. 1, the workstation 104 could be an example of the system 1300 described here, as could the data processing server 116. The system 1300 includes a processor 1310, a memory 1320, a storage device 1330, and one or more input/output interface devices 1340. Each of the components 1310, 1320, 1330, and 1340 can be interconnected, for example, using a system bus 1350.

The processor 1310 is capable of processing instructions for execution within the system 1300. The term "execution" as used here refers to a technique in which program code causes a processor to carry out one or more processor instructions. In some implementations, the processor 1310 is a single-threaded processor. In some implementations, the processor 1310 is a multi-threaded processor. In some implementations, the processor 1310 is a quantum computer. The processor 1310 is capable of processing instructions stored in the memory 1320 or on the storage device 1330. The processor 1310 can execute operations such as the MRI acquisition and image reconstruction techniques described here.

The memory 1320 stores information within the system 1300. In some implementations, the memory 1320 is a computer-readable medium. In some implementations, the memory 1320 is a volatile memory unit. In some implementations, the memory 1320 is a non-volatile memory unit.

The storage device 1330 is capable of providing mass storage for the system 1300. In some implementations, the storage device 1330 is a non-transitory computer-readable medium. In various different implementations, the storage device 1330 can include, for example, a hard disk device, an optical disk device, a solid-state drive, a flash drive, magnetic tape, or some other large capacity storage device. In some implementations, the storage device 1330 can be a cloud storage device, e.g., a logical storage device including one or more physical storage devices distributed on a network and accessed using a network. In some examples, the storage device can store long-term data, such as MR signal data, coil sensitivity profile data, and reconstructed image data, among others. The input/output interface devices 1340 provide input/output operations for the system 1300. In some implementations, the input/output interface devices 1340 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, etc. A network interface device allows the system 1300 to communicate, such as to transmit and receive data. In some implementations, the input/output device can include driver devices configured to receive input data and send output data to other input/output devices, e.g., keyboard, printer and display devices 1360. In some implementations, mobile computing devices, mobile communication devices, and other devices can be used.

The system 1300 can be distributively implemented over a network, such as a server farm, or a set of widely distributed servers or can be implemented in a single virtual device that includes multiple distributed devices that operate in coordination with one another. For example, one of the devices can control the other devices, or the devices can operate under a set of coordinated rules or protocols, or the devices can be coordinated in another fashion. The coordinated operation of the multiple distributed devices presents the appearance of operating as a single device.

In some examples, the system 1300 is contained within a single integrated circuit package. A system 1300 of this kind, in which both a processor 1310 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 1340.

Although an example processing system has been described in FIG. 13, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" can encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the data processing server 116 as shown in FIG. 1) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Other implementations are also within the scope of the following claims.

What is claimed is:

1. A method for imaging a tissue region of a patient, comprising:
   receiving a plurality of magnetic resonance (MR) signals of the tissue region, each MR signal being measured by a corresponding one of a plurality of coils, each coil having a different spatial sensitivity profile; and
   generating an image comprising a plurality of image values of the tissue region based on the plurality of MR signals and the spatial sensitivity profile of each coil, including applying one or more constraints to the image generation, wherein at least one of the constraints applies a coupling between a signal intensity or a spatial sensitivity profile of each of a first image value of the plurality of image values and one or more other image values of the plurality of image values.

2. The method of claim 1, wherein generating the image comprises solving a system of equations subject to the one or more constraints.

3. The method of claim 2, wherein generating the image comprises determining a least squares solution to the system of equations.

4. The method of claim 2, wherein generating the image comprises determining an augmented Lagrangian solution to the system of equations.

5. The method of claim 2, wherein the one or more constraints comprises equality constraints in the system of equations.

6. The method of claim 1, wherein applying the one or more constraints comprises applying a spatial derivative to the plurality of MR signals and the spatial sensitivity profile of each coil.

7. The method of claim 1, wherein applying the one or more constraints comprises applying a filter to the plurality of MR signals and the spatial sensitivity profile of each coil.

8. The method of claim 1, wherein applying the one or more constraints reduces the geometry factor of the image.

9. The method of claim 1, wherein the first image value is associated with a pixel or a voxel of the image.

10. The method of claim 1, wherein the first image value is spatially adjacent to the one or more other image values in the image.

11. The method of claim 1, comprising:
applying a magnetic field to the tissue region of the patient;
generating an excitation RF pulse in the tissue region of the patient; and
measuring MR signal from the tissue region with each of the plurality of coils to produce the plurality of MR signals.

12. The method of claim 11, comprising measuring the tissue region with an acceleration factor greater than or equal to two.

13. The method of claim 11, comprising measuring the tissue region in Cartesian space.

14. The method of claim 11, comprising measuring the tissue region in non-Cartesian space.

15. The method of claim 1, wherein applying the one or more constraints comprises applying a spatial transformation to the plurality of MR signals.

16. The method of claim 1, wherein at least one of the constraints couples a value of a first image generated from MR signals measured by a first subset of the plurality of coils to a value of a second image generated from MR signals measured by a second subset of the plurality of coils, the first subset of coils being different than the second subset of coils.

17. The method of claim 1, wherein applying the one or more constraints comprises relating a first MR signal associated with a first contrast to a second MR signal associated with a second contrast.

18. A computing system comprising:
one or more processors; and
storage encoded with instructions that, when executed by the one or more processors, cause the one or more processors to:
receive a plurality of magnetic resonance (MR) signals of the tissue region, each MR signal being measured by a corresponding one of a plurality of coils, each coil having a different spatial sensitivity profile; and
generate an image comprising a plurality of image values of the tissue region based on the plurality of MR signals and the spatial sensitivity profile of each coil, including applying one or more constraints to the image generation, wherein at least one of the constraints applies a coupling between a signal intensity or a spatial sensitivity profile of each of a first image value to one or more other image values of the plurality of image values.

19. The computing system of claim 18, wherein at least one of the constraints couples a value of a first image generated from MR signals measured by a first subset of the plurality of coils to a value of a second image generated from MR signals measured by a second subset of the plurality of coils, the first subset of coils being different than the second subset of coils.

20. A non-transitory computer readable medium storing instructions for causing a computing system to:
receive a plurality of magnetic resonance (MR) signals of the tissue region, each MR signal being measured by a corresponding one of a plurality of coils, each coil having a different spatial sensitivity profile; and
generate an image comprising a plurality of image values of the tissue region based on the plurality of MR signals and the spatial sensitivity profile of each coil, including applying one or more constraints to the image generation, wherein at least one of the constraints applies a coupling between a signal intensity or a spatial sensitivity profile of each of a first image value to one or more other image values of the plurality of image values.

* * * * *